(12) United States Patent
Ho et al.

(10) Patent No.: US 12,043,668 B2
(45) Date of Patent: Jul. 23, 2024

(54) ANTI-HUMAN CSF-1R ANTIBODY AND USES THEREOF

(71) Applicant: DEVELOPMENT CENTER FOR BIOTECHNOLOGY, Taipei (TW)

(72) Inventors: Chen-Hsuan Ho, Taipei (TW); Chu-Bin Liao, Taipei (TW); Yu-Kai Chen, Taipei (TW); Chen-Wei Huang, Taipei (TW); Tze-Ping Yang, Taipei (TW); Szu-Liang Lai, Taipei (TW)

(73) Assignee: DEVELOPMENT CENTER FOR BIOTECHNOLOGY, Taipei (TW)

( * ) Notice: Subject to any disclaimer, the term of this patent is extended or adjusted under 35 U.S.C. 154(b) by 698 days.

(21) Appl. No.: 17/413,496

(22) PCT Filed: Dec. 13, 2019

(86) PCT No.: PCT/US2019/066384
§ 371 (c)(1),
(2) Date: Jun. 11, 2021

(87) PCT Pub. No.: WO2020/124039
PCT Pub. Date: Jun. 18, 2020

(65) Prior Publication Data
US 2022/0064310 A1  Mar. 3, 2022

Related U.S. Application Data

(60) Provisional application No. 62/779,455, filed on Dec. 13, 2018.

(51) Int. Cl.
*C07K 16/28* (2006.01)
*A61P 35/00* (2006.01)

(52) U.S. Cl.
CPC .......... *C07K 16/2866* (2013.01); *A61P 35/00* (2018.01); *C07K 2317/24* (2013.01); *C07K 2317/31* (2013.01); *C07K 2317/34* (2013.01); *C07K 2317/565* (2013.01); *C07K 2317/76* (2013.01); *C07K 2317/92* (2013.01)

(58) Field of Classification Search
CPC ............ C07K 16/2866; C07K 2317/24; C07K 2317/31; C07K 2317/34; C07K 2317/565; C07K 2317/76; C07K 2317/92; A61P 35/00
See application file for complete search history.

(56) References Cited

U.S. PATENT DOCUMENTS

| | | | |
|---|---|---|---|
| 9,169,323 B2 * | 10/2015 | Fertig | ............ A61P 35/00 |
| 2011/0243947 A1 | 10/2011 | Doody et al. | |
| 2011/0274683 A1 | 11/2011 | Wong et al. | |
| 2014/0314771 A1 | 10/2014 | Hoves | |
| 2018/0258175 A1 | 9/2018 | Lippincott et al. | |

FOREIGN PATENT DOCUMENTS

| | | |
|---|---|---|
| EP | 3108897 A1 | 12/2016 |
| WO | 2006/089549 A1 | 8/2006 |
| WO | 2009/026303 A1 | 2/2009 |
| WO | 2009/112245 A1 | 9/2009 |
| WO | 2011/131407 A1 | 10/2011 |
| WO | 2012/110360 | 8/2012 |
| WO | 2012/110360 A1 | 8/2012 |
| WO | 2012110360 A1 | 8/2012 |
| WO | 2015/028455 | 3/2015 |
| WO | 2015/028455 A1 | 3/2015 |
| WO | 2015/032906 | 3/2015 |
| WO | 2016/097420 A1 | 6/2016 |
| WO | 2016/189045 A1 | 12/2016 |
| WO | 2018/144334 A1 | 8/2018 |

OTHER PUBLICATIONS

Guillermo Arango Duque, et al.: Macrophage cytokines: involvement in immunity and infectious diseases: vol. 5: Article 491: Oct. 2014: pp. 1-12.
Alberto Mantovani, et al.: Macrophage polarization: tumor-associated macrophages as a paradigm for polarized M2 mononuclear phagocytes: Trends in Immunology: vol. 23: No. 11: Nov. 2002: pp. 649-555.
Jeffrey W. Pollard: Role of Colony-Stimulating Factor-1 in Reproduction and Development: Molecular Reproduction and Development: vol. 46: 1997: pp. 54-61.
Xu-Ming Dal, et al.: Targeted disruption of the mouse colony-stimulating factor 1 receptor gene results in osteopetrosis, mononuclear phagocyte deficiency, increased primitive progenitor cell frequencies, and reproductive defects: vol. 99: No. 1: Jan. 1, 2002: pp. 111-120.
Paola Allavena, et al.: The inflammatory micro-environment in tumor progression: The role of tumor-associated macrophages: Critical Reviews in Oncology/Hematology 66 (2008) pp. 1-9.
Alberto Mantovani, et al.: The origin and function of tumor-associated macrophages: Immunology Today: vol. 13: No. 7: 1992: pp. 265-270.

(Continued)

*Primary Examiner* — Brad Duffy
*Assistant Examiner* — Elizabeth A Shupe
(74) *Attorney, Agent, or Firm* — LADAS & PARRY LLP

(57) ABSTRACT

An antibody, or an antigen-binding fragment thereof, that binds specifically to human CSF-1R includes a heavy chain variable domain that contains a HCDR1 region having the sequence of SEQ ID NO: 4, a HCDR2 region having the sequence of SEQ ID NO: 5, and a HCDR3 region having the sequence of SEQ ID NO: 6; and a light chain variable domain that contains a LCDR1 region having the sequence of SEQ ID NO: 7, a LCDR2 region having the sequence of SEQ ID NO: 8, and a LCDR3 region having the sequence of SEQ ID NO: 9. The heavy chain variable domain comprises the sequence of SEQ ID NO: 2, and wherein the light chain variable domain comprises the sequence of SEQ ID NO: 3.

14 Claims, 10 Drawing Sheets
Specification includes a Sequence Listing.

(56) References Cited

OTHER PUBLICATIONS

E. Richard Stanley, et al.: CSF-1 Receptor Signaling in Myeloid Cells: Downloaded from http://cshperspectives.cshlp.org/ at Penn State Univ on Jun. 6, 2014—Published by Cold Spring Harbor Laboratory Press.
Martin B. Pedersen, et al.: High intratumoral macrophage content is an adverse prognostic feature in anaplastic large cell lymphoma: Histopathology 2014, 65, pp. 490-600.
Qiong-wen Zhang, et al.: Prognostic Significance of Tumor-Associated Macrophages in Solid Tumor: A Meta-Analysis of the Literature: Dec. 2012: vol. 7: Issue 12: e50946.
S. Chockalingam, et al.: Macrophage colony-stimulating factor and cancer: a review: Sep. 20, 2014.
E. Richard Stanley, et al.: The Macrophage Colony-Stimulating Factor, CSF-1: vol. 116: 1985: pp. 564-587.
Damya Laoui, et al.: Functional relationship between tumor-associated macrophages and macrophage colony-stimulating factor as contributors to cancer progression: Oct. 2014: vol. 5: Article 489: pp. 1-15.
Johanna A. Joyce, et al.: Microenvironmental regulation of metastasis: vol. 9: Apr. 2009: pp. 239-252.
Bin-Zhi Qian, et al.: Macrophage Diversity Enhances Tumor Progression and Metastasis: Cell 141: Apr. 2, 2010 © 2010 Elsevier Inc. pp 39-51.
Debbie C Strachan, et al.: CSF1R inhibition delays cervical and mammary tumor growth in murine models by attenuating the turnover of tumor-associated macrophages and enhancing infiltration by CD8+ T cells: Oncoimmunology vol. 2: Issue 12: e26968; Dec. 2013; © 2013 Landes Bioscience.
Roy Noy, et al.: Tumor-Associated Macrophages: From Mechanisms to Therapy: Immunity 41: Jul. 17, 2014: Elsevier Inc.: pp. 49-61.
Yu Zhu, et al.: CSF1/CSF1R Blockade Reprograms Tumor-Infiltrating Macrophages and Improves Response to T Cell Checkpoint Immunotherapy in Pancreatic Cancer Models: Downloaded from cancerres.aacrjournals.org on Aug. 11, 2014. © 2014 American Association for Cancer Research.
Stephanie M. Pyonteck, et al.: CSF-1R inhibition alters macrophage polarization and blocks glioma progression: Received Dec. 31, 2012; accepted Aug. 14, 2013; published online Sep. 22, 2013; doi:10.1038/nm.3337.
Jonathan B. Mitchem, et al.: Targeting Tumor-Infiltrating Macrophages Decreases Tumor-Initiating Cells, Relieves Immunosuppression, and Improves Chemotherapeutic Responses: Cancer Res: 73(3) Feb. 1, 2013.
Strachan DC et al., "CSF1R inhibition delays cervical and mammary tumor growth in murine models", OncoImmunology (2013), vol. 2(12), e26968. Landes Bioscience.
Noy R et al., "Tumor-associated macrophages, from mechanisms to therapy", Immunity (2014), vol. 41:49-61, http://dx.doi.org/10.1016/j.immuni.2014.06.010. Elsevier Inc.
Zhu Y et al., "CSF1, CSF1R blockade reprograms tumor-infiltrating macrophages". Cancer Research (2014), doi:10.1158/0008-5472. CAN-13-3723, pp. 1-30. Elsevier Inc.
Pyonteck SM et al., "CSF-1R inhibition alters macrophage polarization and blocks glioma progression", Nature Medicine (2013), doi:10.1038/nm.3337, pp. 1-12.
Mitchem JB et al., "Targeting tumor-infiltrating macrophages decreases tumor-initiating cells", Cancer Research (2013), DOI: 10.1158/0008-5472.CAN-12-2731, pp. 1128-1141.
Office Action dated Sep. 25, 2023 for the corresponding CN Patent Application No. 201980082351.2.
Search Report dated Sep. 25, 2023 for the corresponding Chinese Patent Application No. 201980082351.2.
Research Progress of Macrophage and Tumor Therapy: J Mod Med Health: Jan. 2017: vol. 33: No. 2 (with English abstract).
Office Action issued by the Taiwan Intellectual Property Office (TIPO) on Jan. 14, 2021 for the Taiwan counterpart (Appln. No. 108145750) of the present application including a Partial Translation.
Extended European Search Report (EESR), which was issued by the EPO on Mar. 18, 2022 for the EPO counterpart (Appln. No. EP 19896573.3) of the present application.
Carola H. Ries, et al.: "Targeting Tumor-Associated Macrophases with Anti-CSF-1R Antibody Reveals a Strategy for Cancer Therapy", Cancer Cell, Cell Press, US. vol. 25, No. 6, Jun. 2, 2014, pp. 846-859, XP028855510.
Papadopoulos P. Kyriakos et al.: "First-in-Human Study of AMG 820, a Monoclonal Anti-Colony-Stimulating Factor 1 Receptor Antibody, in Patients with Advanced Solid Tumors", Clinical Cancer Research, vol. 23, No. 19, Oct. 1, 2012, pp. 5703-5710, XP055555062.
Carola H. Ries, et al.: "CSF-1/CSF-1R targeting agents in clinical development for cancer therapy", Current Opinion in Pharmacology, vol. 23, Aug. 1, 2015, pp. 45-51, XP055243143.
Peyraud Florent, et al.: "CSF-14 Inhibitor Development: Current Clinical Status", Current Oncology Reports, vol. 19, No. 11, Sep. 5, 2017, XP055543065.
ISR for International Application PCT/US2019/066384.
Written Opinion for International Application PCT/US2019/066384.
Guillermo Arango Duque, et al.: Macrophage cytokines: involvement in immunity and infectious diseases: Frontiers in Immunology | Molecular Innate Immunity : Oct. 2014: vol. 5: Article 491: pp. 1-12.
Alberto Mantovani, et al.: Macrophage polarization: tumor-associated macrophages as a paradigm for polarized M2 mononuclear phagocytes: Trends in Immunology: vol. 23: No. 11: Nov. 2002: pp. 549-555.
Jeffrey W. Pollard: Role of Colony-Stimulating Factor-1 in Reproduction and Development: Molecular Reproduction and Development 46: pp. 54-61: 1997.
Xu-Ming Dai, et al.: Targeted disruption of the mouse colony-stimulating factor 1 receptor gene results in osteopetrosis, mononuclear phagocyte deficiency, increased primitive progenitor cell frequencies, and reproductive defects: Blood, Jan. 1, 2002: vol. 99: No. 1: pp. 111-120.
E. Richard Stanley, et al.: CSF-1 Receptor Signaling in Myeloid Cells: Downloaded from http://cshperspectives.cshlp.org/ at Penn State Univ on Jun. 6, 2014—Published by Cold Spring Harbor.
Martin B Pedersen, et al.: High intratumoral macrophage content is an adverse prognostic feature in anaplastic large cell lymphoma: Histopathology 2014, 65, pp. 490-500: DOI: 10.1111/his.12407.
Qiong-wen Zhang, et al.: Prognostic Significance of Tumor-Associated Macrophages in Solid Tumor: A Meta-Analysis of the Literature: PLOS One | www.plosone.org. Dec. 2012: vol. 7: Issue 12: e50946: pp. 1-14.
S. Chockalingam, et al.: Macrophage colony-stimulating factor and cancer: a review: Tumor Biol. DOI 10.1007/s13277-014-2627-0: Sep. 20, 2014: pp. 1-10.
E. Richard Stanley: The Macrophage Colony-Stimulating Factor, CSF-1: Methods in Enzymology: vol. 116: 1985: pp. 564-587.
Damya Laoui, et al.: Functional relationship between tumor-associated macrophages and macrophage colony-stimulating factor as contributors to cancer progression: www.frontiersin.org: Oct. 2014: vol. 5: Article 489: pp. 1-16.
Johanna A. Joyce, et al.: Microenvironmental regulation of metastasis: Nature Reviews | Cancer: vol. 9: Apr. 2009: 239: pp. 239-250.
Bin-Zhi Qian, et al.: Macrophage Diversity Enhances Tumor Progression and Metastasis: Cell 141: Apr. 2, 2010: Elsevier Inc: pp. 39-51.

* cited by examiner

N: Negative control (THP-1 only)
P: Positive control (+ rhM-CSF-1)
1: + 5 ug/ml
2: + 0.5 ug/ml

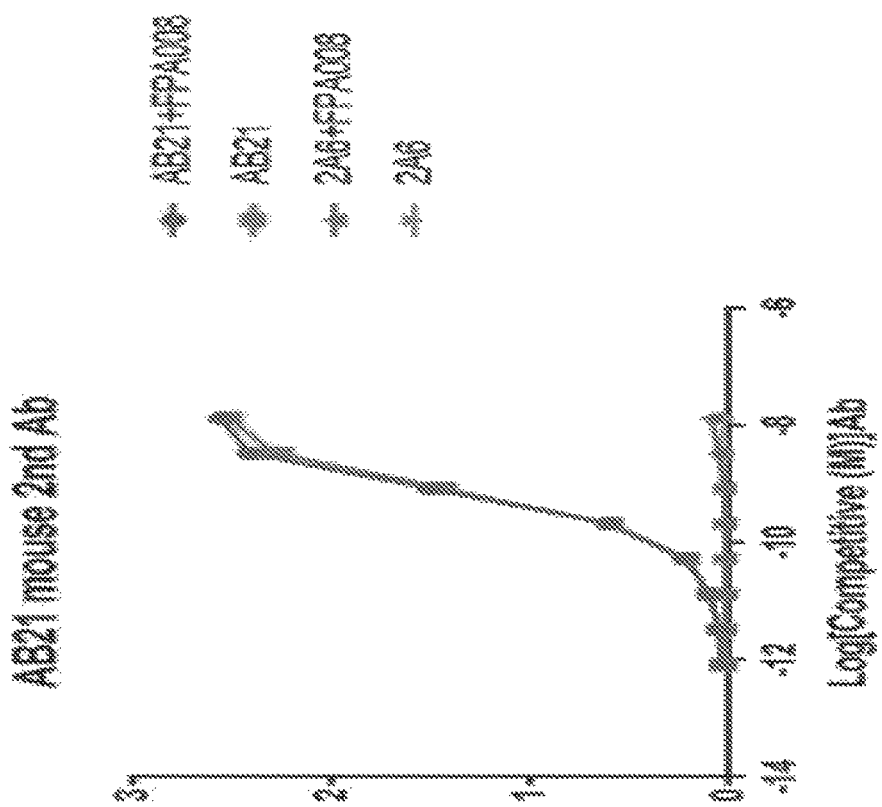
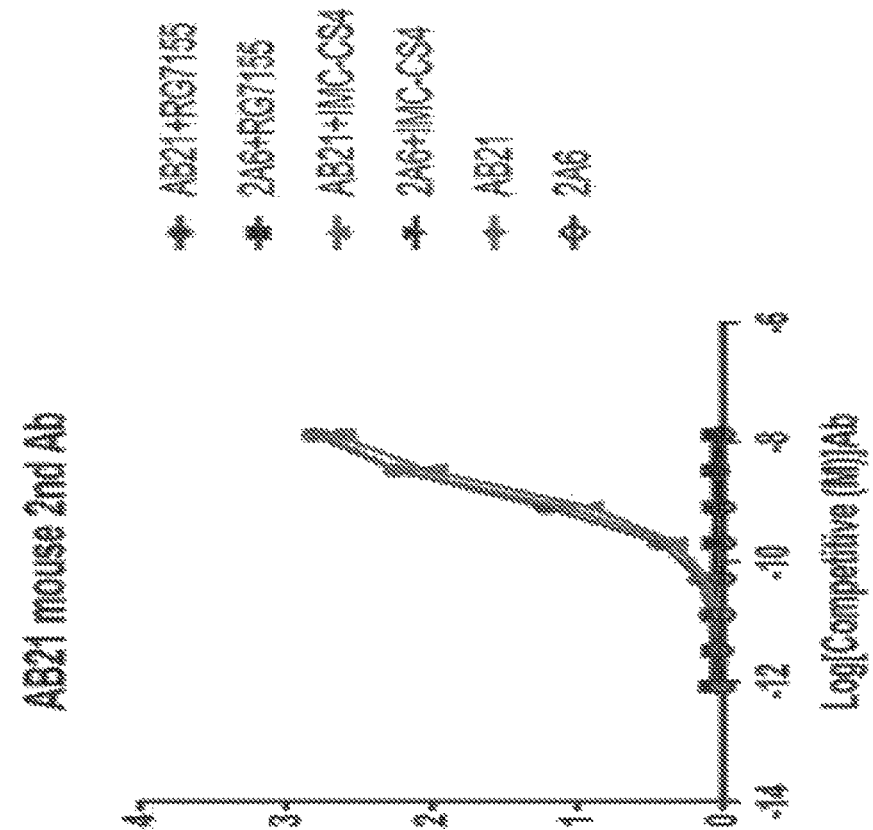
FIG. 7

| Kabat No. | 1 | 22 | HCDR1 | 36 | FR2 | 49 | HCDR2 | 66 | FR3 | 92 | HCDR3 | 103 | FR4 | |
|---|---|---|---|---|---|---|---|---|---|---|---|---|---|---|
| MOUSE AB21 VH | EVQLQQSGPELVKPGASVKISCKAS | | GYSFTGYTMN | | WVKQSHGKSLEWIG | | LINPYNGGTTYNQKFKG | | KATLTVDKSSSTAYMELLSLTSEDSAVYYCAR | | RDGYSGSSYWYFDV | | WGAGTTVTVSS | SEQ ID NO: 2 |
| HU AB21 VH | EVQLVQSGAEVKKPGATVKISCKVS | | GYSFTGYTMN | | WVQQAPGKGLEWIG | | LINPYTGGTTYNQKFKG | | RVTITADTSTDTAYMELSSLRSEDTAVYYCAR | | RDGYSGSSYWYFDV | | WGQGTLVTVSS | SEQ ID NO: 10 |
| HU AB21 VHB1 | EVQLVQSGAEVKKPGATVKISCKVS | | GYSFTGYTMN | | WVQQAPGKGLEWIG | | LINPYTGGTTYNQKFKG | | KATLTVDKSSSTAYMELSSLRSEDTAVYYCAR | | RDGYSGSSYWYFDV | | WGQGTLVTVSS | SEQ ID NO: 11 |
| HU AB21 VHB2 | EVQLVQSGAEVKKPGATVKISCKVS | | GYSFTGYTMN | | WVQQAPGKGLEWIG | | LINPYTGGTTYNQKFKG | | KATLTVDKSSSTAYMELSSLRSEDTAVYYCAR | | RDGYSGSSYWYFDV | | WGQGTLVTVSS | SEQ ID NO: 12 |
| HU AB21 VHB3 | EVQLVQSGAEVKKPGASVKISCKAS | | GYSFTGYTMN | | WVQQAPGKGLEWIG | | LINPYTGGTTYNQKFKG | | KATLTVDKSSSTAYMELSSLRSEDTAVYYCAR | | RDGYSGSSYWYFDV | | WGQGTLVTVSS | SEQ ID NO: 13 |
| SEQ ID NO: 4 | | | GYSFTGYTMN | | | | | | | | | | | |
| SEQ ID NO: 5 | | | | | | | LINPYTGGTTYNQKFKG | | | | | | | |
| SEQ ID NO: 6 | | | | | | | | | | | RDGYSGSSYWYFDV | | | |

FIG. 9A

|  | FR1 | LCDR1 | FR2 | LCDR2 | FR3 | LCDR3 | FR4 |  |
|---|---|---|---|---|---|---|---|---|
| Kabat No. | 1 | 23 | 33 | 49 | 57 | 88 | 98 | |
| MOUSE AB21 VL | DIQMTQSSYLSVSLGGRVTITC | KASEHINKWLA | WYQQKPGNAPRLLIS | GATSLET | GVPSRFSGSGSGRDYTLSITSLQTEDVATYYC | QQYWSTPFT | FGSGTKLEIK | SEQ ID NO: 3 |
| HU AB21 VL | DIQMTQSPSSLSASVGDRVTITC | KASEHINKWLA | WYQQKPGKAPKLLIY | GATSLET | GVPSRFSGSGSGTDYTLTISSLQPEDFATYYC | QQYWSTPFT | FGQGTKVEIK | SEQ ID NO: 14 |
| HU AB21 VL YLB1 | DIQMTQSPSSLSASVGDRVTITC | KASEHINKWLA | WYQQKPGKAPKLLIS | GATSLET | GVPSRFSGSGSGTDYTLTISSLQPEDFATYYC | QQYWSTPFT | FGQGTKVEIK | SEQ ID NO: 15 |
| HU AB21 VL YLB2 | DIQMTQSPSSLSASVGDRVTITC | KASEHINKWLA | WYQQKPGKAPKLLIS | GATSLET | GVPSRFSGSGSGTDYTLTISSLQPEDVATYYC | QQYWSTPFT | FGSGTKLEIK | SEQ ID NO: 16 |

SEQ ID NO: 7  KASEHINKWLA

SEQ ID NO: 8  GATSLET

SEQ ID NO: 9  QQYWSTPFT

FIG. 9B

Humanized Design

Ab21 Heavy chain

| Name | Frame work | Back mutation site | Count |
|---|---|---|---|
| M | Mouse | All mouse | |
| Hu | IGHV1-69*2*01 | No back mutation | |
| Hu-B1 | | 66, 67, 69, 71, 73, 76, 93 | 7 Back |
| Hu-B2 | | 37, 38, 48, 66, 67, 69, 71, 73, 76, 93 | 10 Back |
| Hu-B3 | | 17, 24, 38, 48, 66, 67, 69, 71, 73, 75, 76, 84, 93 | 13 Back |

Ab21 Light chain

| Name | Frame work | Back mutation | Count |
|---|---|---|---|
| M | Mouse | All mouse | |
| Hu | IGKV1-NL1*01 | No back mutation | |
| Hu-B1 | | 15, 85 | 2 Back |
| Hu-B2 | | 15, 17, 66, 80, 83 | 5 Back |

FIG. 10

| Name | Name | Name | ul Purify | mg/ml conc. | mg Amount | ug/ml Yield | Bmax | ELISA Kd(M) |
|---|---|---|---|---|---|---|---|---|
| | M (IgG1) | M | 280 | 0.036 | 10.08 | 0.17 | | |
| | B1(IgG1) | Hu | 220 | 0.3547 | 78.03 | 1.30 | | |
| M-M(IgG4) | | | 230 | 0.3993 | 91.84 | 1.53 | 3.195 | |
| Hu-Hu(IgG4) | | | 220 | 2.5507 | 561.15 | 9.35 | | 8.30E-08 |
| B1-Hu(IgG4) | | | 210 | 2.1458 | 450.62 | 7.51 | 3.195 | |
| B2-Hu(IgG4) | | | 190 | 3.2885 | 624.82 | 10.41 | 3.171 | |
| B3-Hu(IgG4) | | | 170 | 2.2047 | 374.80 | 6.25 | | |
| B3-B1(IgG4) | | | 280 | 1.1185 | 313.18 | 5.22 | 3.046 | |

ANTI-HUMAN CSF-1R ANTIBODY AND USES THEREOF

This application is a national phase entry under 35 USC 371 of International Patent Application No. PCT/US2019/066384 filed on 13 Dec. 2019, which claims the benefit of U.S. Application No. 62/779,455 filed on 13 Dec. 2018, the entire contents of which are incorporated by reference.

BACKGROUND OF INVENTION

Field of the Invention

The invention relates generally to antibodies that can specifically neutralize human CSF-1R and methods for their use and preparation. In particular, the invention relates to antibodies, which may possess macrophage reducing effects, the manufacture and use of such antibodies in treating diseases associated with abnormal macrophage proliferation, such as tumor.

Background Art

CSF-1R (M-CSFR) is a cell surface receptor for the macrophage colony stimulating factor (M-CSF or CSF-1) and IL-34 Binding of CSF-1 to its receptor activates signal transduction pathways, including PI3K/Akt and MAPK pathways, resulting in proliferation, survival, motility, and differentiation of cells of the monocyte/macrophage lineage. CSF-1R is expressed by hematopoietic stem cell, myeloid cells, including monocytes macrophages, osteoclasts, dendritic cells and microglia, neural progenitor cells. Myeloid cells are heterogeneous and multifunctional cells that play important roles in both innate immunity and acquired immunity. High plasticity and diversity are characteristic of macrophage lineages. Macrophages can differentiate into different phenotypes and have different biological functions depending on the microenvironment and metabolic states. In rodents and humans, macrophages have two major activation phenotypes, M1 (classical or pro-inflammatory) and M2 (alternative or anti-inflammatory) phenotypes (Mantovani A et al, 2002). M2 macrophages secrete anti-inflammatory cytokines, and their functions relate to tissue repairs and angiogenesis.

Elevated expression or activation of CSF-1R and/or its ligand has been found in a variety of cancers, and elevated levels of M-CSF are associated with poor prognosis in certain cancers (Pedersen M B et al., 2017; Zhang Q W et al, 2012). M-CSF is one of several cytokines implicated in the recruitment of tumor-associated macrophages (TAMs), which exhibit similar characteristics to M2 macrophages and contribute to tumor angiogenesis and tumor progression to metastasis. Activation of CSF-1R also leads to proliferation and differentiation of osteoclast precursors, thereby mediating the process of bone resorption. Inhibition of CSF-1R therefore provides treatments of cancers, especially cancer invasion, angiogenesis, metastasis, immunotolerance, and bone metastases. Because of its role in osteoclast biology, CSF-1R is also an important therapeutic target for osteoporosis, inflammatory arthritis, and other inflammatory bone erosion. Targeting TAM through CSF-1R signaling by neutralizing antibody is therefore an attractive strategy to treat oncological and inflammatory/immunological diseases.

SUMMARY OF INVENTION

Embodiments of the invention relate to antibodies, or binding fragments thereof, that bind specifically to human CSF-1R. The antibodies include humanized antibodies and human antibodies. In one aspect, the present invention relates to antibodies that specifically bind to human CSF-1R extracellular domain (ECD) (SEQ ID NO. 1). An antibody of the invention comprises a heavy chain variable region sequence that includes HCDR1, HCDR2, and HCDR3, wherein the HCDR1 sequence is GYSFTGYNMN (SEQ ID NO: 4), the HCDR2 sequence is NIDPYYGGT-TYNQKFKG (SEQ ID NO: 5), the HCDR3 sequence is GDYSGSSYWYFDV (SEQ ID NO: 6), wherein the HCDR sequences are defined according to the method of Kabat. In accordance with some embodiments of the invention, a heavy chain variable region of an antibody that specifically binds human CSF-1R has the sequence of SEQ ID NO: 2.

In another aspect, the present application relates to antibodies that specifically bind human CSF-1R, comprising a light chain variable region having LCDR1, LCDR2 and LCDR3 sequences, wherein said LCDR1 sequence is KAS-DHINNWLA (SEQ ID NO: 7), the LCDR2 sequence is GATSLET (SEQ ID NO: 8), the LCDR3 sequence is QQNNEDPLT (SEQ ID NO: 9), wherein the LCDR sequences are defined according to the method of Kabat. In accordance with some embodiments of the invention, a light-chain variable region of an antibody that specifically binds human CSF-1R has the sequence of SEQ ID NO: 3.

In another aspect, the present invention relates to an antibody that specifically binds human CSF-1R, comprising a heavy chain variable region having HCDR1, HCDR2, and HCDR3 and a light chain variable region having LCDR1, LCDR2 and LCDR3, wherein the HCDR1 sequence is GYSFTGYNMN (SEQ ID NO: 4), the HCDR2 sequence is NIDPYYGGTTYNQKFKG (SEQ ID NO:5), the HCDR3 sequence is GDYSGSSYWYFDV (SEQ ID NO:6), the LCDR1 sequence is KASDHINNWLA (SEQ ID NO. 7), the LCDR2 sequence is GATSLET (SEQ ID NO: 8), the LCDR3 sequence is QQYWSTPFT (SEQ ID NO: 9), and wherein the HCDR and LCDR sequences are defined according to method of Kabat.

In some embodiments, a heavy-chain variable region of an antibody that specifically binds human CSF-1R has the sequence of SEQ ID NO: 2, and a light-chain variable region of the antibody that specifically binds human CSF-1R has the sequence of SEQ ID NO: 3.

In some embodiments of the invention, an antibody that specifically binds human CSF-1R is a full antibody, an Fab fragment, an F(ab')2 fragment, or an ScFv fragment.

In some embodiments, an antibody that specifically binds human CSF-1R is a fully human antibody.

In some embodiments, an antibody that specifically binds human CSF-1R further comprises a heavy chain constant region selected from IgG1, IgG2, or IgG4 isoforms and a light chain constant region selected from κ subtype or λ isoform.

In some embodiments, an antibody (or a binding fragment thereof) of the invention forms part of a bispecific or multi-specific antibody by conjugating with another specific binding domain for a second target. In some embodiments, an antibody (or a binding fragment thereof) of the invention forms part of an antibody-drug conjugate (ADC) by conjugating with a drug (payload). The drug or payload may be selected for its ability to modulate the CSF-1R-expressing cells.

Another aspect of the present invention relates to a pharmaceutical composition for treating a disease mediated by CSF-1R, wherein the pharmaceutical composition, wherein the pharmaceutical composition comprises a therapeutically effective amount of an antibody that specifically binds to the human CSF-1R, or a binding fragment thereof. A therapeutically effective amount is an amount sufficient to produce the desired therapeutic outcome. One skilled in the art would appreciate that a therapeutically effective amount would depend on the disease conditions, the patient (gender, age, physical condition, etc.), route of administration, etc. One skilled in the art would be able to identify such an amount without undue experimentation.

Another aspect of the present invention relates to uses of a pharmaceutical composition comprising an antibody, or a binding fragment thereof, that specifically binds human CSF-1R for the treatment and/or prophylaxis of diseases mediated by the CSF-1R, CSF-1, and/or IL-34.

In some embodiments, the CSF-1R, CSF-1, and/or IL-34 mediated disease is cancer.

In some embodiments, cancers include, but are not limited to, multiple myeloma, leukemia, (e.g., acute myeloid leukemia (AML) and chronic myeloid leukemia (CML)), prostate cancer, glioblastoma multiforme, giant cell tumor of bone, giant cell tumor of the tendon sheath, metastasis of tumors to other tissues, and gastrointestinal stromal tumor melanoma, non-small cell lung cancer, renal cancer, breast cancer, leukemia, ovarian cancer, myelofibrosis, gastrointestinal stromal tumor, and other advanced solid tumors.

In some embodiments, the CSF-1R, CSF-1, and/or IL-34 mediated disease is an inflammatory or immunological disease.

In some embodiments, the inflammatory or immunological disease is pigmented villonodular synovitis (PVNS), osteoporosis, inflammatory arthritis, or other inflammatory bone erosion.

BRIEF DESCRIPTION OF DRAWINGS

FIG. 7 illustrates the competition ELISA of mAb AB21 with other CSF-1R antibodies.

FIG. 9A shows heavy chain variable regions of anti-CSF-1R antibody variants of the invention. The locations of CDR1, CDR2, CDR3, FR1, FR2, FR3, and FR4 are shown.

FIG. 9B shows light chain variable regions of anti-CSF-1R antibody variants of the invention. The locations of CDR1, CDR2, CDR3, FR1, FR2, FR3, and FR4 are shown.

FIG. 10 shows Tables illustrating the residues of back mutations of antibodies of the invention.

FIG. 11 shows expression and characterization results of various anti-CSF-1R antibody variants of the invention.

DETAILED DESCRIPTION

Figure 1:
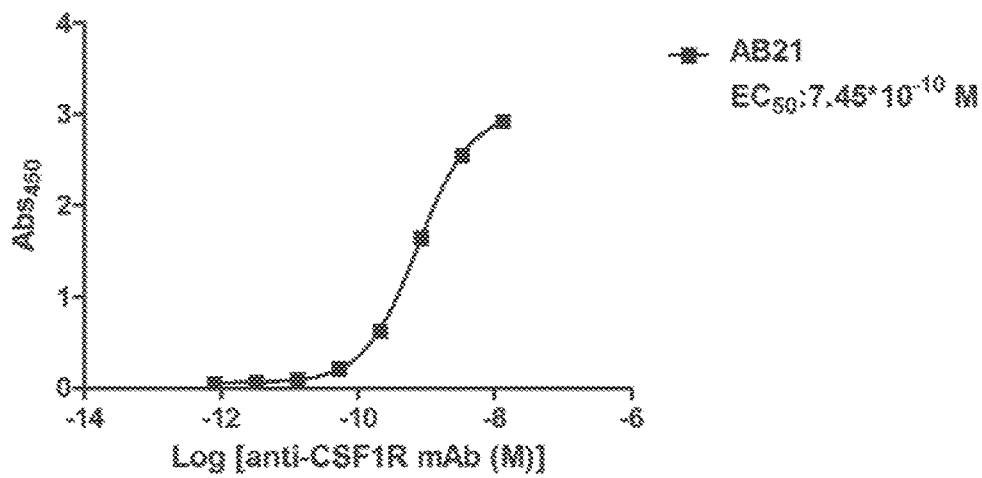
FIG. 1 illustrates the binding of mAb AB21 antibody to CSF-1R by ELISA.

Embodiments of the invention relate to novel antibodies that can bind specific to human CSF-1R with high affinities and can deliver therapeutic benefits to a subject. The antibodies may be humanized antibodies or human antibodies. In some embodiments, an anti-CSF-1R antibodies can potently neutralize CSF-1R signaling that is induced by CSF-1 and/or induced by IL-34 The antibodies of the invention, which may be human or humanized antibodies, can be used as therapeutics for treating a variety of disorders mediated by CSF-1R, which are more fully described herein.

Some embodiments of the invention relate to the use of anti-CSF-1R antibodies, or antigen-binding fragments thereof, for the diagnosis, assessment, and treatment of diseases or disorders associated with CSF-1R, CSF-1, and/or IL-34, or aberrant expression thereof. The subject antibodies are used in the treatment or prevention of neoplasms and/or the treatment or prevention of autoimmune and/or inflammatory diseases, among other diseases.

Particularly, an antibody or antigen-binding fragment thereof, according to embodiments of the invention can bind specifically to an epitope in human CSF-1R extracellular domain (ECD) or a fragment thereof, wherein the human CSF-1R extracellular domain (ECD) has the amino acid sequence of SEQ ID NO: 1, and the epitope is located in a region spanning residues 228-233: Serine-228, Valine-229, Aspartic acid-230, Valine-231, Asparagine-232, and Phenylalanine-233. That is, the epitope is located in $^{228}$Ser-Val-Asp-Val-Asn-Phe$^{233}$ (SEQ ID NO:17).

An antibody according to embodiments of the invention can be full-length (for example, an IgG1 or IgG4 antibody), or may comprise only an antigen-binding fragment/portion thereof (for example, a Fab, F(ab')2, or scFv fragment), and may be modified to improve functionalities as needed.

An antibody, or antigen-binding fragment thereof, according to embodiments of the invention specifically binds to human CSF-1R. The human CSF-1 receptor (CSF-1R; colony stimulating factor 1 receptor; synonyms: M-CSF receptor; Macrophage colony-stimulating factor 1 receptor, Fms proto-oncogene, c-fms, SEQ ID NO:1), also known as CD115, is a single pass type I membrane protein encoded by a proto-oncogene c-fms with 972 amino acids and a predicted molecular weight of 107 kilo Daltons. It acts as the receptor for colony stimulating factor 1 (CSF-1 or M-CSF), a cytokine which controls the proliferation, differentiation and functional of macrophages. A second ligand for CSF-1R, interleukin-34 (IL-34), was identified in 2008.

The role of CSF-1R may involve immune responses, bone remodeling and in the reproductive system because knockout mice for either CSF-1 (Pollard, J. W., Mol. Reprod. Dev. 46 (1997) 54-61) or CSF-1R. (Dai, X. M., et al., Blood 99 (2002) 111-120) have been shown to have osteopetrotic, hematopoietic, tissue macrophage, and/or reproductive phenotypes.

The main biological effects of CSF-1R signaling include the differentiation, proliferation, migration, and survival of hematopoietic precursor cells to cells of the macrophage lineage, such as macrophages, osteoclasts, and microglia. Binding of CSF-1 (M-CSF) to CSF-1R induces the formation of homodimers and activation of the kinase by tyrosine phosphorylation, leading to further downstream PI3K, AKT, and MAPK signalings.

The term "antibody" as used herein means any antigen-binding molecule or molecular complex comprising at least one complementarity determining region (CDR) that specifically binds to or interacts with a particular antigen (e.g., CSF-1R). The term "antibody" includes immunoglobulin molecules, comprising four polypeptide chains, two heavy (H) chains and two light (L) chains inter-connected by disulfide bonds, as well as multimers thereof. Each heavy chain comprises a heavy chain variable region (VH) and a heavy chain constant region, comprising three domains, CH1, CH2 and CH3. Each light chain comprises a light chain variable region (VL) and a light chain constant region (CL1). The VH and VL regions can be further subdivided into complementarity determining regions (CDRs), interspersed with framework regions (FR). Each VH and VL is composed of three CDRs and four FRs, arranged from amino-terminus to carboxy-terminus in the following order: FR1, CDR1, FR2, CDR2, FR3, CDR3, FR4. In different embodiments of the invention, the FRs may be identical to the human germline sequences or may be naturally or artificially modified.

The term "antigen-binding portion" or "antigen-binding fragment" of an antibody, and the like, as used herein, includes any naturally occurring, enzymatically obtainable, synthetic, or genetically engineered polypeptide or glycoprotein that specifically binds an antigen to form a complex. An antigen binding fragment of an antibody may be derived from full antibody molecules using any suitable standard techniques, such as proteolytic digestion or recombinant genetic engineering techniques Non-limiting examples of an antigen-binding fragment includes: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, Nanobodies® (e.g. monovalent Nanobodies®, bivalent Nanobodies®, etc.), small modular immunopharmaceuticals (SMIPs), and shark variable IgNAR domains, are also encompassed within the expression "antigen-binding fragment," as used herein.

An antigen-binding fragment of an antibody typically comprises at least one variable domain. The variable domain may be of any size or amino acid composition and will generally comprise at least one CDR, which is adjacent to or in frame with one or more framework sequences. In antigen-binding fragments having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding fragment of an antibody may contain a monomeric VH or VL domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) VH-CH1; (ii) VH-CH2; (iii) VH-CH3; (iv) VH-CH1-CH2; (v) VH-CH1-CH2-CH3, (vi) VH-CH2-CH3, (vii) VH-CL; (vii) VL-CH1; (ix) VL-CH2; (x) VL-CH3, (xi) VL-CH1-CH2; (xii) VL-CH1-CH2-CH3; (xiii) VL-CH2-CH3; and (xiv) VL-CL. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric VH or VL domain (e.g., by disulfide bond(s).

As with a full antibody molecule, an antigen-binding fragment may be monospecific or multi-specific (e.g., bispecific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bispecific antibody formats disclosed herein, may be adapted for use in the context of an antigen-binding fragment of an antibody of the present invention using routine techniques available in the art.

Antibodies of the invention may be used as antibody-drug conjugates (ADCs), which can specifically target CSF-1R. The conjugates on the ADCs may modulate the immune cells that express CSF-1R or cells that interact with cells that express CSF-1R (e.g., CSF-1R expressing cells). These ADCs can use any antibody of the invention, or an antigen-binding fragment thereof. The drugs (payloads) that are conjugated to the antibody (or binding fragment) can be any that are commonly used in ADCs. The methods for conjugation can be those known in the art.

Preferably, an antibody or antigen-binding fragment thereof according to embodiments of the invention is a mammalian antibody. The term "mammalian antibody", as used herein, is intended to include antibodies having variable and constant regions derived from mammalian germline immunoglobulin sequences. The mammalian antibodies of the invention may include amino acid residues not encoded by mammalian germline immunoglobulin sequences (e.g., mutations introduced by random or site-specific mutagenesis in vitro or by somatic mutation in vivo), for example in the CDRs, in particular CDR3, or other regions.

The term "recombinant mammalian antibody" as used herein, is intended to include all mammalian antibodies that are prepared, expressed, created or isolated by recombinant means, such as antibodies expressed using a recombinant expression vector transfected into a host cell (described further below), antibodies isolated from a recombinant, combinatorial mammalian antibody library (described further below), antibodies isolated from an animal (e.g., a mouse) that is transgenic for mammalian immunoglobulin genes or antibodies prepared, expressed, created or isolated by any other means that involves splicing of mammalian immunoglobulin gene sequences to other DNA sequences. Such recombinant mammalian antibodies have variable and constant regions derived from mammalian germline immunoglobulin sequences. In certain embodiments, however, such recombinant mammalian antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the mammalian antibody germline repertoire in vivo.

Mammalian antibodies such as human antibodies can exist in two forms that are associated with hinge heterogeneity. In one form, an immunoglobulin molecule comprises a stable four chain construct of approximately 150-160 kDa, in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody) These forms have been extremely difficult to separate, even after affinity purification.

The anti-CSF-1R antibodies, or antigen-binding fragments, disclosed herein may comprise one or more amino acid substitutions, insertions and/or deletions in the framework and/or CDR regions of the heavy and/or light chain variable domains, as compared to the corresponding germline sequences, from which the antibodies were derived. The present invention includes an antibody, and an antigen-binding fragment thereof, which is derived from any of the amino acid sequences disclosed herein, wherein one or more amino acids within one or more framework and/or CDR regions may be mutated to the corresponding residue(s) of the germline sequence, from which the antibody was derived, or to the corresponding residue(s) of another mammalian germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments, which comprise one or more individual germline mutations or combinations thereof.

In certain embodiments, one or more of the framework and/or CDR residues within the VH and/or VL domains may be mutated back to the residues found in the original germline sequences, from which the antibody was derived. In other embodiments, only certain residues may be mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) may be mutated to the corresponding residue(s) of a different germline sequence (i.e., a germline sequence that is different from the germline sequence from which the antibody was originally derived).

Furthermore, the antibodies of the present invention may contain any combination of two or more germline mutations within the framework and/or CDR regions. e.g., wherein certain individual residues are mutated to the corresponding residue of a particular germline sequence, while certain other residues that differ from the original germline sequence are maintained or are mutated to the corresponding residues of a different germline sequence. Once obtained, antibodies and antigen-binding fragments that contain one or more germline mutations can be easily tested for one or more desired properties, such as improved binding specificity, increased binding affinity, improved or enhanced antagonistic or agonistic biological properties (as the case may be), reduced immunogenicity, etc. Antibodies and antigen-binding fragments obtained in this general manner are encompassed within the scope of the present invention.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99%, of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical/physical properties (e.g., charge of hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine, (6) acidic side chains, aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Best fit which can be used with default parameters to determine sequence homology or sequence identity between closely related polypeptides, such as homologous polypeptides from different species of organisms or between a wild type protein and a mutant thereof. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res 25:3389-402, each herein incorporated by reference.

In preferred embodiments of the invention, an antibody or antigen-binding fragment thereof comprises complementarity determining regions of a heavy chain variable region and complementarity determining regions of a light chain variable region, wherein the complementarity determining regions of the heavy chain variable region comprises CDRH1 (or HCDR1), CDRH2 (or HCDR2) and CDRH3 (or HCDR3) regions, and the complementarity determining regions of the light chain variable region comprises CDRL1 (or LCDR1), CDRL2 (or LCDR2) and CDRL3 (or LCDR3) regions.

In accordance with some embodiments of the invention, the CDRH1 region comprises the amino acid sequence of SEQ ID NO: 4, or a substantially similar sequence thereof having at least 90%, at least 95%, at least 98% or at least 99% sequence identity; the CDRH2 region comprises the amino acid sequence of SEQ ID NO: 5, or a substantially similar sequence thereof having at least 90%, at least 95%, at least 98% or at least 99% sequence identity; the CDRH3 region comprises the amino acid sequence of SEQ ID NO: 6, or a substantially similar sequence thereof having at least 90%, at least 95%, at least 98% or at least 99% sequence identity: the CDRL1 region comprises the amino acid sequence of SEQ ID NO: 7, or a substantially similar sequence thereof having at least 90%, at least 95%, at least 98% or at least 99% sequence identity; the CDRL2 region comprises the amino acid sequence of SEQ ID NO: 8, or a substantially similar sequence thereof having at least 90%, at least 95%, at least 98% or at least 99% sequence identity; and the CDRL3 region comprises the amino acid sequence of SEQ ID NO: 9, or a substantially similar sequence thereof having at least 90%, at least 95%, at least 98% or at least 99% sequence identity.

In accordance with preferred embodiments of the invention, an anti-CSF-1R antibody, or an antigen-binding fragment thereof, comprises a heavy chain variable region comprising the amino acid sequences of SEQ ID NO:2 or a substantially similar sequence thereof having at least 90%, at least 95%, at least 98% or at least 99% sequence identity. Preferably, the heavy chain variable region is encoded by a nucleic acid sequence of SEQ ID NO:2. The anti-CSF-1R antibody, or an antigen-binding fragment thereof, comprises a light chain variable region comprising the amino acid sequence of SEQ ID NO: 3 or a substantially similar sequence thereof having at least 90%, at least 9596, at least 98% or at least 99% sequence identity or a substantially similar sequence thereof. Preferably, the light chain variable region is encoded by a nucleic acid sequence of SEQ ID NO: 3.

Antibodies of the invention were confirmed to have specific bindings with CSF-1R via ELISA or BIAcore assay. Briefly, for ELISA, CSF-1R was coated on a 96-well ELISA plate (1 µg/ml). After binding of anti-CSF-1R antibodies, a goat anti mouse IgG conjugated with horse radish peroxidase (HRP) was used as a second antibody and 3,3',5,5'-Tetramethylbenzidine (TMB) was used as a substrate to assess the antibody-CSF-1R bindings. The OD450 was read to calculate the activities.

Figure 2:
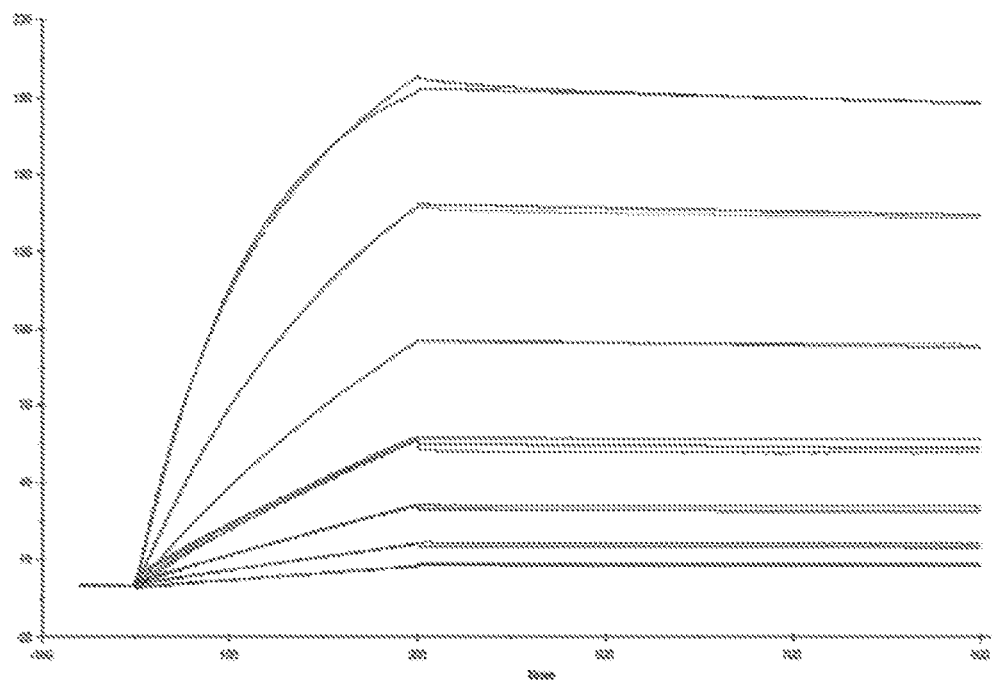
FIG. 2 illustrates binding of mAb AB21 to human CSF-1R by Biacore analysis.

As shown in FIG. 1 (ELISA) and FIG. 2 (BIAcore), a mouse hybridoma anti-human CSF-1R antibody (mAb AB21) showed specific bindings with CSF-1R. FIG. 1 shows results from ELISA assay, in which M-CSF R/CD115 Fc chimera (from R&D Systems. Inc., Minneapolis, MN) was coated in 96-wells and mAb AB21 at various concentrations was added. After binding and washing, the bound mAb AB21 was assessed using a horseradish peroxidase conjugated secondary antibody. The results show that mAb binds to this antigen with a high affinity (Kd around 0.745 nM). FIG. 2 shows similar results from Biacore assay.

A useful antibody against CSF-1R should block the bindings between CSF-1 and CSF-1R. Whether mAb AB21 can block the bindings between CSF-1 and CSF-1R was assessed with an ELISA-based assay. Briefly, the CSF-1R ECD was coated overnight in a 96-well plate at concentration of 1.2 µg/ml. The wells were then washed and blocked with 1% blocking buffer. After wash, serial diluted antibodies were added, and then the CSF-1 ligand (100 ng/ml) was added into wells. After antibody blocking, a human M-CSF-biotinylated antibody and Streptavidin peroxidase (POD) conjugate were used as secondary antibody and 3,3',5,5'-tetramethylbenzidine (TMB) was used as a substrate to assess the blocking activity of anti-CSF-1R antibody. The OD450 was read to calculate the activities.

Figure 3:
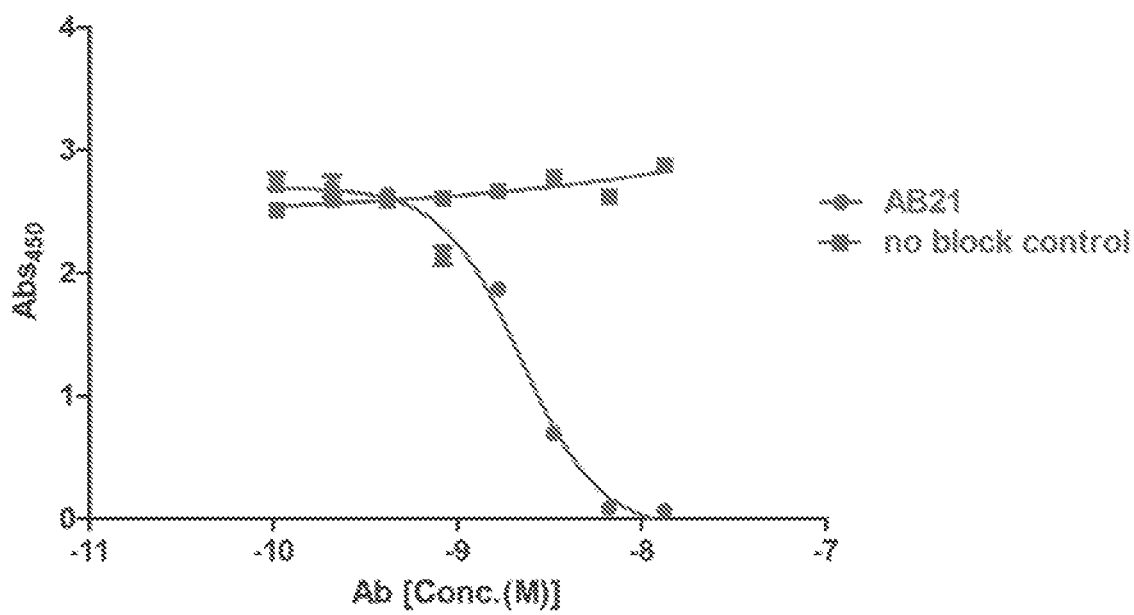
FIG. 3 illustrates the ability of mAb AB21 to block the binding between CSF-1 to CSF-1R.

As shown in FIG. 3, mAb AB21 of the invention shows specific and potent activities that block CSF-1/CSF-1R interactions. These results confirm that antibody of the invention would be effective in suppressing the proliferation and differentiation of tumor-associated macrophages mediated by CSF-1 and CSF-1R signaling.

Figure 4:
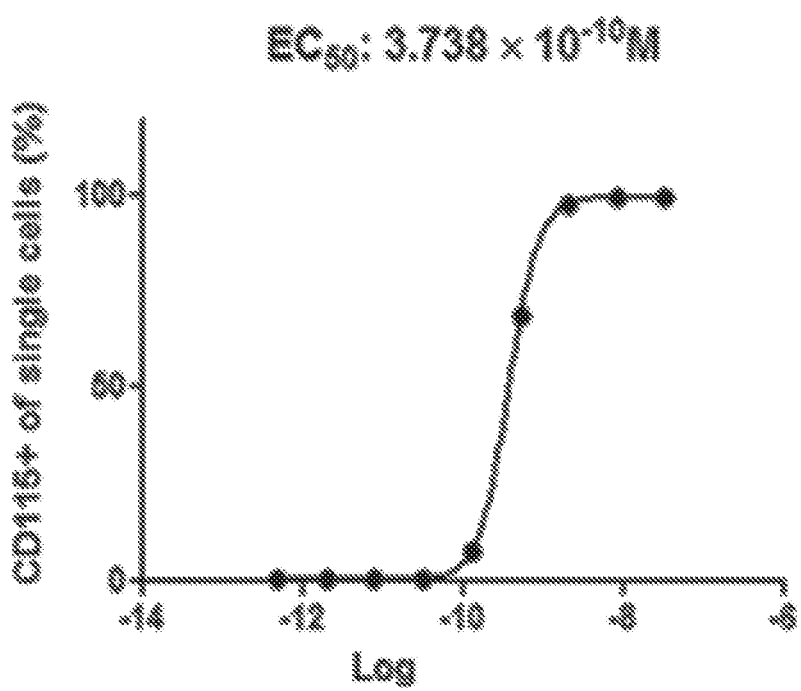
FIG. 4 illustrates the binding ability of mAb AB21 to CSF-1R on cell surface by flow cytometry.

In addition to the ELISA assay, anti-CSF-1R antibody binding to CSF-1R expressing cells can also be assayed by Flow Cytometry using THP-1 cell line, a human monocytic cell line, which expresses CSF-1R endogenously. Briefly, THP-1 cells were incubated with anti-CSF-1R antibodies for 1 hour, then analyzed using flow cytometry. As shown in FIG. 4, mAb of the invention AB21 can bind THP-1 cells in a specific manner, indicating that this antibody can recognize CSF-1R on cell surfaces.

The above results clearly indicate that anti-CSF-1R antibodies of the invention can bind CSF-1R with high affinities, both in vitro and on cell surfaces. Therefore, these antibodies should be able to modify cellular activities medicated by CSF-1R. The following examples prove that indeed these antibodies can interfere with the interactions between CSF-1 and CSF-1R interactions, leading to interruption of CSF-1R-mediated signaling and subsequent cellular functions/activities.

Growth Inhibition of Ba/F3-CSF-1R Cells Under Treatment with Anti-CSF-1R Monoclonal Antibody.

Full-length human CSF-1R gene was stably expressed in Ba/F3 cells line (DSMZ, Germany), and cultured in RPMI-1640 supplemented with 10% fetal bovine (Biological Industries, 04-121-1A) and recombinant human M-CSF (R&D systems). The growth of this cell line is dependent on recombinant human IL-3, CSF-1, and IL-34 (all from R&D systems). To assess the in vivo activity of the antibodies of the invention, $8 \times 10^3$ Ba/F3-CSF-1R cells were seeded in each well of a 96-well-plate and incubated for 3 days in the presence of different concentrations of antibodies in order to determine an IC50 (concentration with 50 percent inhibition of cell viability). A human antibody constant region fragment (hFc) was used as a negative control. The MTS (Promega CellTiter 96® Aqueous MTS reagent powder) and Phenazine methosulfate (PMS) (Sigma Aldrich, P9625) assay system was used to detect cell viability by measuring the absorbance of the cells MTS (3-(4,5-dimethylthiazol-2-yl)-S-(3-carboxymethoxyphenyl)-2-(4-sulfophenyl)-2H-tetrazolium), in the presence of phenazine methosulfate (PMS), produces a formazan product that has an absorbance maximum at 490 nm in phosphate-buffered saline.

Figure 5:
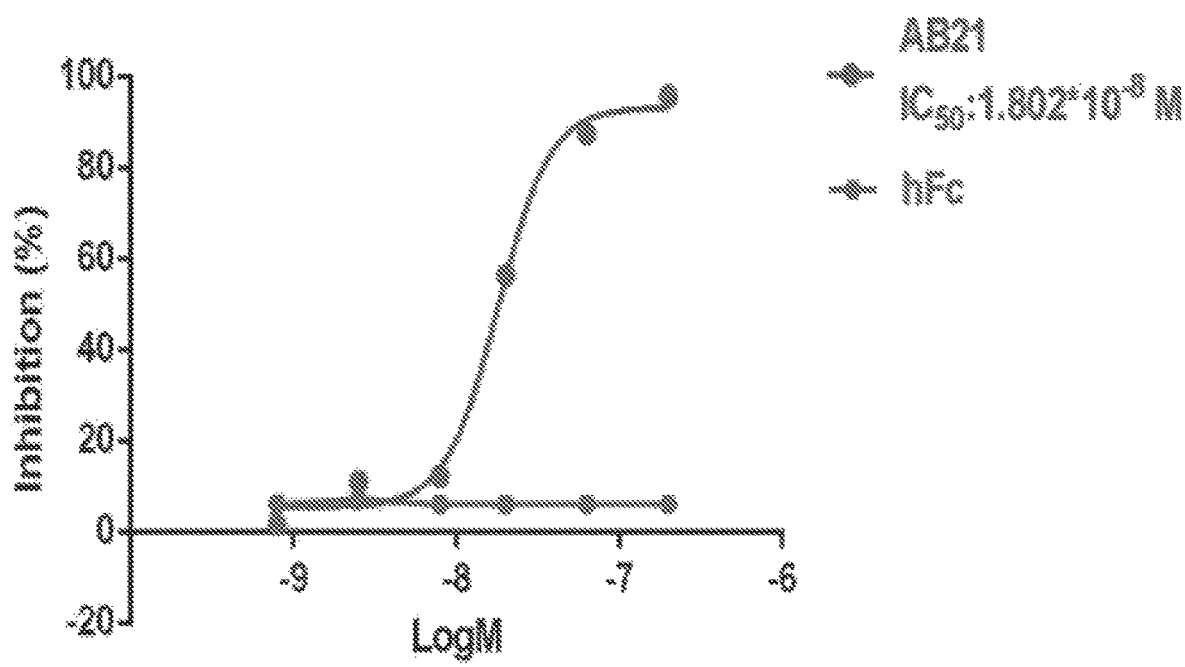
FIG. 5 illustrates the ability of mAb AB21 to inhibit CSF-1-dependent cell growth of Ba/F3-CSF-1R cell line.

As shown in FIG. 5, anti-CSF-1R antibody, mAb AB21, of this invention can block the interactions between CSF-1 and CSF-1R, thereby inhibiting the growth of CSF-1-dependent Ba/F3-CSF-1R cells. These results indicate that antibodies of the invention would be useful in vivo for the treatment of CSF-1R mediated diseases.

Anti-CSF-1R Monoclonal Antibody Treatment Downregulates the Down-Stream Signaling of CSF-1R.

Figure 6:
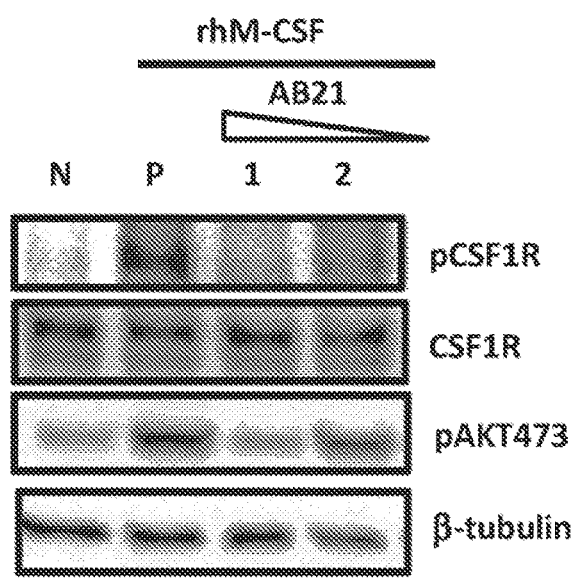
FIG. 6 illustrates the ability of mAb AB21 to block CSF-1R downstream signaling.

Impacts of binding of anti-CSF-1R to CSF-1R on downstream signaling of CSF-1R were analyzed by western blot. THP-1 or Ba/F3-CSF-1R cells, cultured with or without recombinant human M-CSF (rhM-CSF), were treated with high and low doses of mAb AB21. As shown in FIG. 6, mAb AB21 can inhibit the phosphorylation of CSF-1R and AKT, which is a kinase downstream of CSF-1R signaling, in a dose-dependent manner. These results indicate that antibodies of the invention can indeed suppress CSF-1R mediated signaling. Thus, antibodies of the invention should be useful for the treatment of diseases mediated by CSF-1R.

Anti-CSF-1R Monoclonal Antibody AB21 Binds to a Different Epitope from Those of Other Anti-CSF-1R Monoclonal Antibodies in Clinical Trials.

There are several anti-CSF-1R antibodies on the market. Whether antibodies of the present invention bind to the same epitopes can be investigated with competition assays. Briefly, ELISA Binding assay of mAb AB21 were analyzed in the presence of other anti-CSF-1R monoclonal antibodies in clinical trials such as RG7155 (Roche), FPA008 (Five Prime) and IMC-CS4 (Eli Lilly). As shown in FIG. 7, none of these antibodies can prevent or influence the binding of mAb AB21 to CSF-1R. These results indicate that the binding epitope of mAb AB21 is different from those of RG7155, FPA008, and IMC-CS4.

Binding Epitopes Analysis of Anti-CSF-1R Monoclonal Antibody AB21

Figure 8:
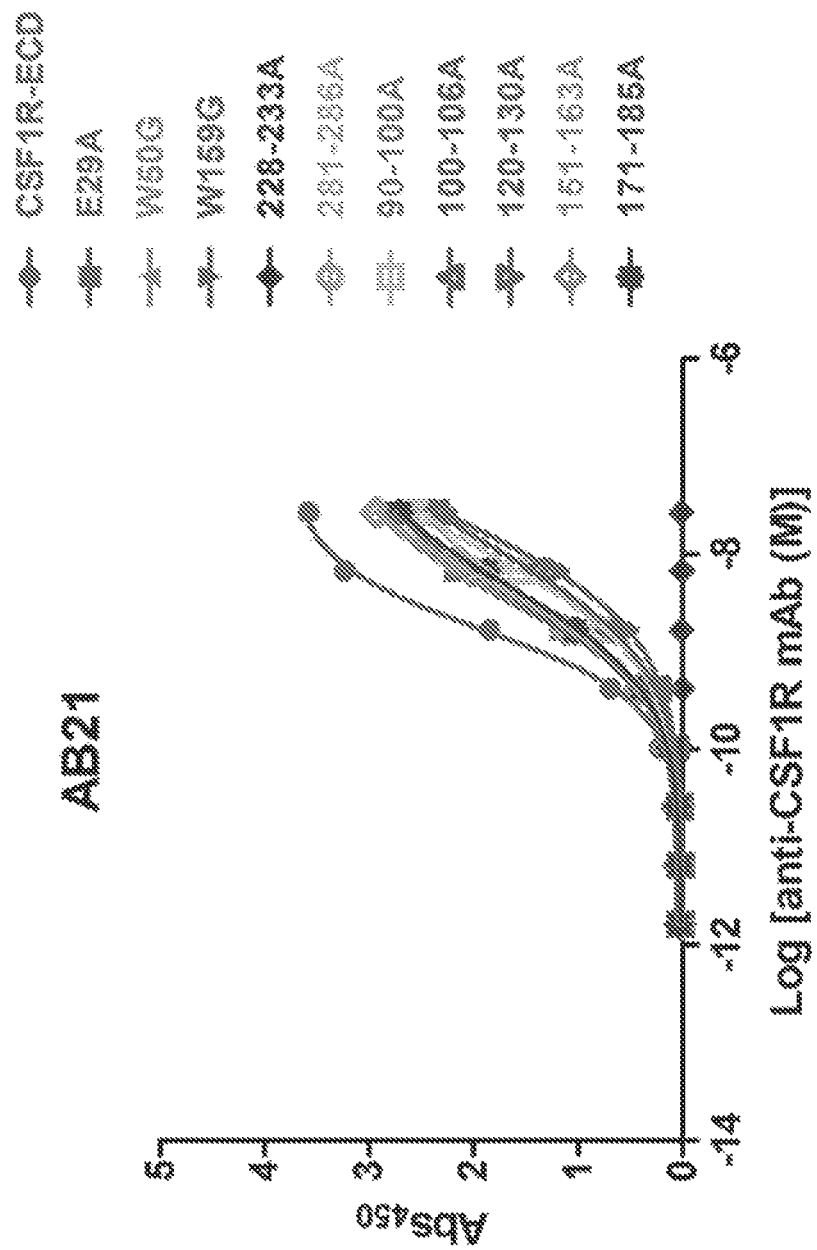
FIG. 8 illustrates the binding epitopes of mAb AB21.

To elucidate the binding epitope for mAb AB21, ELISA assay of mAb AB21 bindings to different CSF-1R ECD mutants created by single point mutations or fragment mutations was performed. Ten (10) different CSF-1R extracellular domain (ECD) mutants were created: E29A, W50G, W159G, 90-100A, 100-106A, 120-130A, 151-163A, 171-185A, 228-233A, and 281-286A, which carry either a single Ala mutation at the indicated location of a stretch of Ala mutations in the indicated regions. As shown in FIG. 8, only the ECD fragment with 228-233 mutations lost mAb AB21's binding, suggesting that the residues at 228-233 are critical for mAb 21 binding to CSF-1R ECD. All other ECD mutants tested retain mAb 21 bindings, suggesting that mutations at these residues would not impact mAb 21 binding to CSF-1R ECD. These results indicate that the epitope of anti-CSF-1R monoclonal antibody mAb AB21 is situated in the region spanning residues 228-233.

The above examples clearly show that anti-CSF-1R antibody AB21 of the invention can bind human CSF-1R specifically and tightly. These antibodies can also interfere with the interactions between CSF-1 and CSF-1R and blocks the CSF-1/CSF-1R bindings, thereby inhibiting CSF-1/CSF-1R mediated signaling. As a result, antibodies of the invention may be used as therapeutics for treating diseases mediated by CSF-1/CSF-1R interactions Such diseases include, for example, cancers and inflammatory/immunological diseases. Examples of cancers include, but are not limited to, lung cancer, breast cancer, prostate cancer, colorectal cancer, etc.

Some embodiments of the invention relate to methods for treating a disease mediated by CSF-1R, such diseases may include cancer. To demonstrate the utility of antibodies of the invention in treating cancers, a murine model was used. Briefly, RKO cells were injected subcutaneously into IL-6 NOG mice (Taconic) which had been engrafted with human PBMC to reconstitute human immune system. On days 8, 15 and 22, the mice were treated with antibodies (e.g., mAB21) of the invention at 30 mpk (mg/Kg), or 10 mpk, or 30 mpk combine with 5 mpk of pembrolizumab (Keytruda) each time. An IgG (not anti-CSF-1R) was used as a control. The tumor growths in various treatment groups were monitored until day 33.

Figure 13:
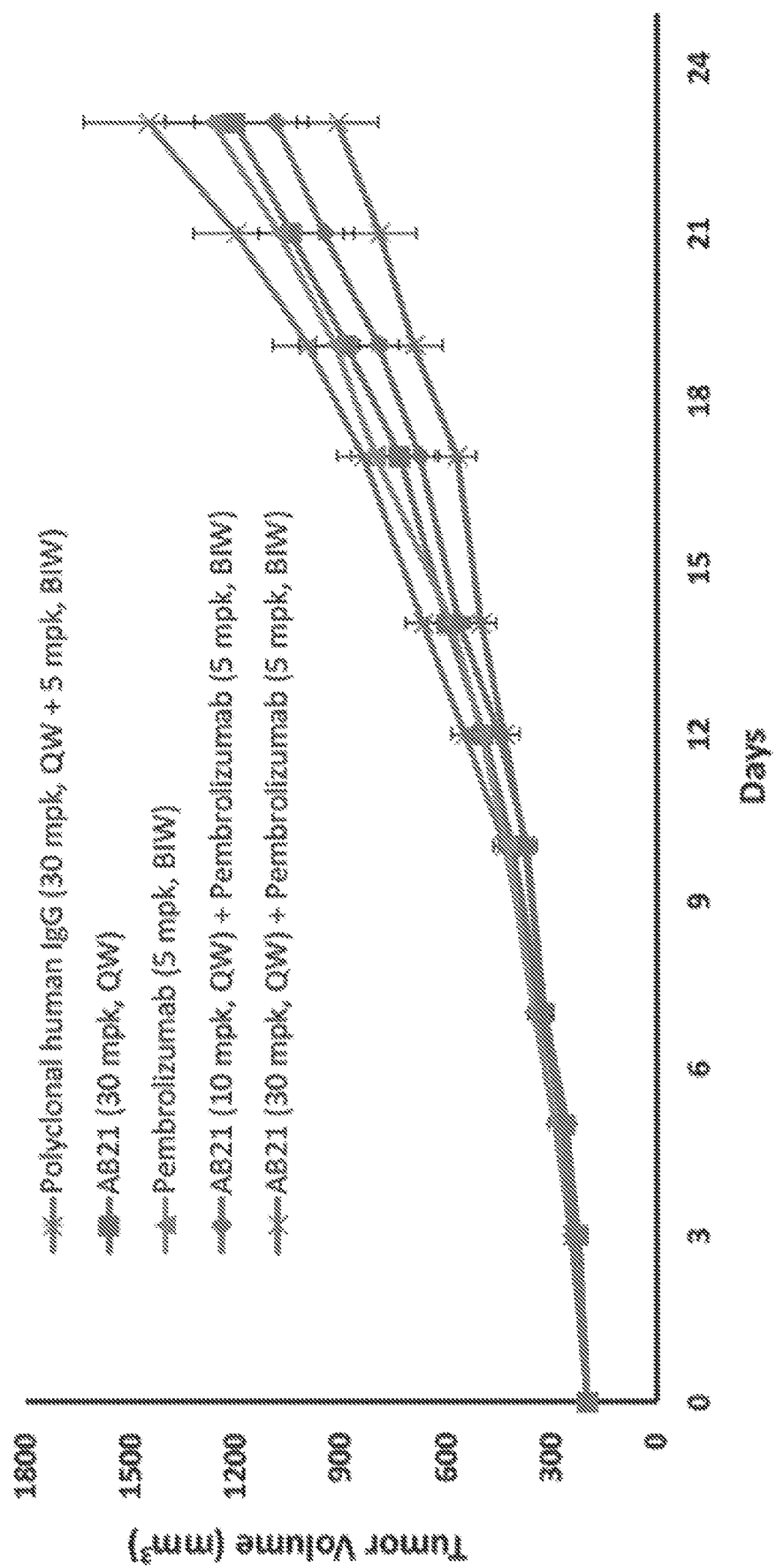
FIG. 13 shows results of inhibition of human RKO colorectal carcinoma by anti-CSF-1R antibody of the invention, as well as combination therapy with an anti-PD-1 antibody, Pembrolizumab. The combination therapy produced a synergistic effect.

As shown in FIG. 13, anti-CSF-1R mAb of the invention was effective in the treatment of cancer in this in vivo colorectal cancer model and with potential to combine with checkpoint inhibitor These results clearly demonstrate that antibody of the invention will be useful for clinical uses to treat cancers.

Some embodiments of the invention relate to methods for treating a disease mediated by CSF-1R, such diseases may include cancer. Some embodiments of the invention relate to methods for treating inflammatory/immunological diseases.

Embodiments of the invention will be further illustrated with the following examples. One skilled in the art would appreciate that these examples are for illustration only and are not meant to limit the scope of the invention and that other modifications and variations are possible without departing from the scope of the invention.

EXAMPLES

Example 1. The CSF-1R Binding ELISA of AB21 Monoclonal Antibody

To evaluate the binding affinity of anti-human CSF-1R antibody AB21 mAb, the hybridomas were grown in IMDM containing 15% fetal calf serum (FCS). After one week culture, $1 \times 10^6$ cells were collected, washed with PBS, resuspended in 200 μl RPMI medium, and injected into severe combined immunodeficiency (SCID) mice by IP injection. Three weeks later, ascites of mice was collected and diluted to 15 ml. Antibody was further purified by 40% ammonium sulfate and Protein A column (Montage antibody purification kit Millipore). The purified antibody was concentrated with an Amicon Ultra-15 centrifugal filter device, following the protocols provided by the manufacturer (Millipore). The purity of antibody was analyzed by 12% SDS PAGE.

One hundred (100) ng of human CSF-1R-Fc protein was coated on a 96-well ELISA plate, and the plate was further washed with PBS. Serial dilutions from $1 \times 10^{-12}$ to $1 \times 10^{-8}$ M of AB21 mAb antibody were added to the plate, and the plate was incubated at 37° C. for 1 hour. A goat anti-mouse IgG conjugated with horseradish peroxidase (HRP) was added After 1 hour, 3,3',5,5'-Tetramethylbenzidine (TMB) was added and OD450 was read. Every study was repeated three times. Data were presented as mean±SD. OD readings and concentrations of antibodies were used to make a multiple scatter plot using GraphPad Prism 5. The values were predicted by four parameter logistic fit.

The results of this experiment are shown in FIG. 1. The Kd value of AB21 mAb antibody was $7.45 \times 10^{-10}$ M (N>3). This result indicates that AB21 mAb antibody can recognize the human CSF-1R protein and has a favorable affinity with a Kd value of about $7.45 \times 10^{-10}$ M.

Example 2. Determination of the Affinity of Anti-CSF-1R Antibody to CSF-1R Using BIAcore Instrument: BIACORE® T200; Chip: 222; Coupling: amine coupling; Buffer: PBS (Biacore BR-1006-72)

To know the biding kinetics difference among individual antibodies, surface plasmon resonance (SPR) measurement with a BIAcore T200 (BIAcore, Inc., Piscataway, N.J.) was used as previously described (Karlsson & Fait, (1997) J. Immunol Methods 200:121-133). Carboxymethylated dextran biosensor chips (CMS, BIAcore Inc.) were activated with N-ethyl-N'-(3-dimethylaminopropyl)-carbodiimide hydrochloride (EDC) and N-hydroxy succinimide (NHS) according to the supplier's instructions. AB21 mAb was diluted with 10 mM sodium acetate, pH 4.8, into 5 microgram/ml before injection at a flow rate of 20 micro L/minute to achieve approximately 100 response units (RU) of coupled protein followed by the injection of 1M ethanolamine to block unreacted groups. For kinetics measurements, two-fold serial dilutions of CSF-1R-ECD (0.3125 nM to 40 nM) were injected in HBS-P BIAcore running buffer provided by the manufacturer (BIAcore, Inc., Piscataway, N.J.) at 25° C. at a flow rate of 30 µL/min, and binding responses on the AB21 mAb were corrected by subtraction of responses on a blank flow cell. Association rates (kon or ka) and dissociation rates (koff or kd) were calculated using a simple one-to-one Langmuir binding model with separate fittings of kon and koff was used. (BIAcore™ Evaluation Software version 3.2).

The results are shown in the FIG. 2. The kon and koff of AB21 mAb binding with CSF-1R are $3.99 \times 10^5$ and $4.90 \times 10^{-5}$, respectively, and $K_d$ is $1.228 \times 10^{-10}$ mol/L.

Example 3. Inhibition of CSF-1 Binding to CSF-1R (ELISA)

CSF-1R-ECD-human Fc (in house) is diluted to 1.2 µg/ml with coating buffer and coating overnight at 4° C. After incubation step, plates were washed 1 time with the wash buffer and blocking with 1% casein blocking buffer at room temperature for 2 hours Different dilutions of purified AB21 antibodies were incubated with 250 ng/ml of M-CSF (R&D system, 216-GMP-025) in dilution buffer at 37° C. for 1 hour. After 5 times of wash, the ligand which bound to the receptor can be detected by 50 ng/ml biotinylated anti-CSF-1 clone BAF216 (R&D Systems, UK) and 1:5000 diluted streptavidin HRP (Roche Diagnostics GmbH, DE, Cat.No. 110891S3001) after 1 hour incubation. Anti CSF-1R SC 2-4A5 (Santa Cruz Biotechnology, US), which inhibits the ligand-receptor interaction, was used as positive control. Plates were developed with TMB Microwell Peroxidase Substrate (KPL, 95059-154) Absorbance was measured at 450 mm. A decrease of absorbance is found if the anti-CSF-1R antibody causes a release of CSF-1 from the dimeric complex. As shown in FIG. 3, anti-CSF-1R antibody AB21 showed significant inhibition of the CSF-1 interaction with CSF-1R, indicating that AB21 mAb can effectively block CSF-1 ligand binding to CSF-1R. These results suggest that the antibodies of the invention can be used to block CSF-1R mediated biological actions. Therefore, antibodies of the invention can be used to prevent or treat diseases mediated by CSF-1R or CSF-1

Example 4 Flow Cytometry Affinity

In addition to binding CSF-1R ECD in vitro, antibodies of the invention can also bind CSF-1R on cells. In this example, THP-1 cells (human monocytic cell line, ATCC® TIB-202™) were stained in different concentrations of antibodies (AB21) from 6 to 0.625 µg/ml. After washing, cells were stained with secondary antibody FITC anti-mouse (1:500 dilution). Cells were fixed with a fixation buffer (FluroFix™ buffer, Biolegend) and analyzed with LSR-Fortessa FACS analyzer (Becton Dickson, US). The FACS analysis results are shown in FIG. 4, which shows a dose-dependent binding of AB 21 mAb. The dose-dependent binding fits a sigmoid curve in the semi-log plot, indicating binding to a specific site (i.e., the antibody binds specifically to the target on the THP-1 cells). The binding curve also show a binding constant of $3.738 \times 10^{-10}$ M.

Example 5. Growth Inhibition of Ba/F3-hCSF-1R Recombinant Cells Under Treatment with Anti-CSF-1R Monoclonal Antibodies To assess the capability of AB21 mAb to inhibit the CSF-1R activity of CSF-1 growth dependent cells, a murine pro-B cell line Ba/F3 (DSMZ Cat. No. ACC 300) was stably transfected with human CSF-1R to render the growth of Ba/F3-hCSF-1R human CSF-1-dependent. Ba/F3-hCSF-1R cells were maintained in RPMI containing 10% FCS with 30 ng/ml recombinant human M-CSF (rhM-CSF, R&D system, 216-MC) $8 \times 10^3$ of Ba/F3-hCSF-1R cells were seeded in a 96-well plate overnight. The cells were incubated for 3 days in the presence of different concentrations of the test antibody in order to determine an IC50 (concentration with 50 percent inhibition of cell viability). A human antibody Fc fragment was used as a negative control. Mix 2 mL of MTS solution (CellTiter 960, Promega) and 100 µL PMS solution (Sigma Aldrich, P9625), and 20 µL of mixed solution were added in each well, incubate at 37° C. for 3 hours, absorbance at 690 µm and 490 nm were measured with a plate reader (Thermo Fisher, Multiscan Go). The inhibition rate of anti-CSF-1R antibody was calculated as: Inhibition rate (%)=[1−(Ab 490-690 nm of experimental group)/(average Ab 490-690 nm of control group)]×100. The IC50 were analyzed by nonlinear regression using GraphPad Prism 5. The results of this experiment are shown in FIG. 5. The results show that AB21 mAb can inhibit the growth of Ba/F3-hCSF-1R in a specific and dose-dependent manner, as evidenced by the sigmoidal curve in the % inhibition vs. concentration semi-log plot.

Example 6. Inhibition of CSF-1-Induced CSF-1R Phosphorylation by Anti-CSF-1R Antibody THP-1 cells were maintained in RPMI 1640 (Gibco, 11875-093) containing 10% FCS. Cells were cultured in rhM-CSF-1-free medium for one day before signaling study. $3 \times 10^6$ cells were resuspended in 1 ml of rhM-CSF-1 free medium with different concentrations (0.5 µg/ml and 5 µg/ml) of AB21 antibody, cultured at 37° C. for 2 hours, and then the cells were stimulated with 20 ng/ml rhM-CSF-1 for 5 minutes at 37° C. rhM-CSF-1 only (without AB21) is used as a positive control. After the incubation, cells were washed with PBS and treated with 200 µL of 2× Sample buffer at 95° C. for 10 minutes. The presence of phosphorylated and total CSF-1 receptor and other CSF-1R downstream signaling proteins in the cell lysate was analyzed with western blotting. The following detection antibodies were used: Rabbit Anti-CSF1R (Santa Cruz, sc-692) (1:500), Rabbit Anti-Phospho-AKT (Ser473) (Cell Signaling, 4060) (1:1000), Mouse Anti-β-tubulin (1-5000) (Abcam, ab6049) The results shown in FIG. 6 clearly demonstrate that AB21 can inhibit the downstream signaling of CSF-1R pathway, as evidenced by the reduced phosphorylation of pAKT473 by AB21 mAb in a dose-dependent manner. These results suggest that the antibodies of the invention can be used to block CSF-1R mediated biological actions Therefore, antibodies of the invention can be used to prevent or treat diseases mediated by CSF-1R or CSF-1.

Example 7. The Competition Assay of Anti-CSF-1R Ab AB21 with Anti-CSF-1R Ab in Clinical Trials Several anti-CSF-1R antibodies are on the market and in clinical trials. To test whether AB21 mAb can compete with these known antibodies, 1 µg/ml of CSF-1R-ECD-hFc were coated in 96-well-plate at 4° C. overnight. Flicking the contents of the plate into the sink and add blocking buffer 100 µl/well to block the non-specific binding. Incubate at room temperature for at least 1 hour. Flicking the contents of the plate into the sink and wash wells three times with 300 µl washing buffer. Add primary antibody in blocking buffer (1 µg/mL for RG7155, 0.25 µg/mL for IMC-CS4) 100 µl/well and incubation at 37° C. for 1 hour. 2A6 was used as a negative control antibody that does not recognize human CSF-1R. Flicking the contents of the plate into the sink and wash wells three times with 300 µl washing buffer. 100 µl/well of 4-fold serial diluted competition antibody in the blocking buffer (the highest conc. is 2 µg/ml) were added and incubation at 37° C. for 1 hour. Wells were washed three times with 300 µl washing buffer. The substrate solution (TMB) were added 100 µl/well and reaction at RT for 20 min and the reaction were stop with 100 µl 1N HCL. The plates were measured with 450 nm absorbance and the $EC_{50}$ value were calculated through GraphPad Prism 5.

The results in FIG. 7 shows that the binding of AB21 mAb is not interfered with by these anti-CSF-1R antibodies (RG7155, FPA008, IMC-CS4) that are being used in clinical trials. These results suggest that AB21 mAb binds to CSF-1R ECD at an epitope different from those of these other antibodies. Therefore, antibodies of the invention may be useful as alternative therapeutics when other antibodies become ineffective due to CSF-1R mutations that abolish their bindings.

Example 8. Epitope Mapping of Anti-CSF-1R Antibody AB21 Versus Clinical Trial Antibodies To determine the binding epitopes of anti-CSF-1R antibody AB21, different CSF-1R extracellular domain variants that certain residues were replaced with alanine were constructed. The CSF-1R ECD variants including E29A, W50G, W159G, 90-100A, 100-106A, 120-130A, 151-163A, 171-185A, 228-233A, and 281-286A. After the variant proteins were purified, the binding affinity of AB21 mAb to these CSF-1R-ECD variants were analyzed by ELISA with the process described in Example 1. The results shown in FIG. 8 demonstrate that the binding epitope for AB21 mAb is located at residues 228-233 in human CSF-1R because only the 228-233A variant of CSF-1R ECD lost binding with AB21 mAb.

Example 9. Cloning of the Gene Encoding the Antibody AB21 mAb was Performed in Accordance with the Methods Described Below (1) cDNA Cloning of Antibody Genes and Preparation The hybridoma was cultured in IMDM medium (manufactured by Gibco) containing 15% FCS. After the cell number reached about $10 \times 10^6$/ml, the cells were collected by centrifugation, and then TRIzol® (manufactured by Invitrogen) was added to extract total RNA in accordance the instruction manual. Cloning of the variable region of the antibody cDNAs was performed using a mouse Ig-primer set (manufactured by Novagen) in accordance with the attached instruction manual.

(a) The synthesis of 1st strand cDNA was performed in accordance with the instruction manual of Superscript® III First-Strand Synthesis System (manufactured by Invitro gen). The first strand cDNA was prepared using 5 µg of the total RNA as a template. Five micrograms of total hybridoma RNA, 1 µL of 50 ng/µL of oligo dT primers, and 1 µL of 10 mM dNTP were mixed, and DEPC-treated water was added to 10 µL in a 200 µL PCR tube. The reaction mixture was incubated at 65° C. for 5 min, and then placed on ice for at least 1 minute. Ten µL of cDNA Synthesis Mixture containing 2 µL of 10×RT buffer, 4 µL of 25 mM $MgCl_2$, 2 µL of DTT, 1 µL of 4 unit RNaseOUT™, and 1 µL of 200 unit Superscript® III RT were added, mixed gently, and collected by brief centrifugation. The reaction tube was incubated for 10 min at 25° C. and followed by 50 min at 50° C. The reaction was terminated at 85° C. for 5 min and chilled on ice. The tube was briefly centrifuged to collect the reaction product, and 1 µL of RNase H was added and incubated for 20 min at 37° C.

(b) Amplification by PCR of Heavy Chain Genes and Light Chain Genes

Add polyG reaction (TdT reaction): cDNA and 10×TdT buffer TdT enzyme (Terminal deoxynucleotidyl transferase, NEB M0315L), $CoCl_2$, and dGTP (Life; R0161) 37° C. for 30 min.

RACE PCR: Heavy and Light chains were amplified by Poly C and 3' reverse primer (AS1 and AS2) (shown in Table. 1).

TABLE I

| 3' Reverse primer list | | |
|---|---|---|
| Mus Heavy AS1 | GCAGCAGATCCAGGGGCCAG | SEQ ID NO: 18 |
| Mus Heavy AS2 | GTGGATAGACAGATGGGG | SEQ ID NO: 19 |
| Mus & Rattus Light Lambda AS1 | GAAATCAGACACACCAGTG | SEQ ID NO: 20 |
| Mus & Rattus t Light Lambda AS2 | GTGGGAGTGGACTTGGGCTG | SEQ ID NO: 21 |
| Mus & Cricetulus IgKV AS1 | GATGTCTTTGGGGTAGAAGTTGTTC | SEQ ID NO: 22 |
| Mus & Cricetulus IgKV AS2 | CTGCTCACTGGATGGTGGGAAGATGG | SEQ ID NO: 23 |

Mouse AS primer was designed according to the published Kurosawa et al. BMC Biology 2012, 10:80. PCR reaction solution having a composition of 5 µL of cDNA, 5 µL of 10× reaction Buffer, 1 µL of 10 mM dNTP mix, 1 µL of 2.5 unit Taq polymerase, and 1 μL of forward primer 1 and 1 μL of reverse primer 2 provided by the primer set was prepared in a final volume of 50 μL with double distilled water and subjected to PCR. For amplification of the light chain and heavy chain of an antibody, a cycle of 94° C. for 10 minutes was used, then a cycle of 94° C. for one minute, 52° C. for 1 minute, and 72° C. for 1 minute was repeated 35 times, and the reaction was incubated at 72° C. for 10 more minutes. The reaction solution was subjected to 2% agarose gel electrophoresis to analyze the reaction products. Products with the correct molecular weights, about 600 bps for the heavy chain (with an on-translation region) and about 500 bps for the light chain (with an un-translation region), were ligated to a TA cloning vector (pJET), and sequencings by T7P primers were then used to determine the nucleotide sequences. Based on the sequence information, antibody sequences were translated into proteins sequences by ExPASY-Translation Tool Resulting sequences of AB21 mAb comprise a heavy chain amino acid sequence and a light chain sequence having complementary determining regions (CDRs), which were determined by the method published by Kabat et ah, Sequences of Proteins of Immunological Interest, Fifth Edition, NIH Publication 91-3242, Bethesda Md (1991), Vols. 1-3.

FIG. 9A depicts the variable heavy chain region/domain amino acid sequence of AB21 mAb (SEQ ID NO: 2). The framework regions (FR1, FR2, FR3, and FR4) and CDRs (HCDR1 (SEQ ID NO: 4), HCDR2 (SEQ ID NO: 5), and HCDR3 (SEQ ID NO: 6)) are indicated. FIG. 9B depicts the variable light chain region/domain amino acid sequences of AB21 mAb (SEQ ID NO: 3). The framework regions (FR1, FR2, FR3, and FR4) and CDRs (LCDR1 (SEQ ID NO: 7), LCDR2 (SEQ ID NO: 8) and LCDR3 (SEQ ID NO: 9)) are indicated.

Example 10. Humanization of AB21 mAb

Selection of Human V Region Framework Sequences

Using mouse monoclonal antibody AB21 mAb as the parent antibody, AB21 mAb CDR sequences according to the Kabat definitions were described in the FIGS. 9A and 9B (SEQ ID NO: 2 and SEQ ID NO: 3).

For humanized AB21 mAb IMGT, human germline VL and VH sequences with the highest degree of homology with the AB21 mAb framework regions were identified from the IMGT database (the International immunogenetics Information System®). The homology searches may be performed with BLAST or similar methods.

As shown in FIG. 9A, the framework sequences of Hu AB21 VH (SEQ ID NO: 10) adapted from IMGT class IGHV1-69-2*01 human heavy chain framework regions differ from those in AB21 mAb by 25 amino acids (the underlined residues), which corresponds to a 30.48% (25/82 total residues in the framework regions) variation. The human light chain framework (kappa I subtype: IGKV1-NL1*01) sequences were identified from IMGT. As shown in FIG. 9B, the sequences of Hu AB21 VL (SEQ ID NO. 14) differ from those in AB21 mAb by 17 amino acids (the underlined residues), which corresponds to a 22.36% (17/76 total residues in the framework regions) variation.

Back Mutation

Grafting of CDR onto frameworks results in variable domains (VH and VL) from IMGT sources may not have the optimal sequences. Therefore, affinities of the antibodies may not be the best. Indeed, the initial humanized antibody (Hu-Hu in FIG. 11) has a $K_d$ of $8.3 \times 10^{-8}$ M, while the original mouse antibody (M-M in FIG. 11) has a $K_d$ of $9.36 \times 10^{-11}$ M. This represents a drop of about 1000 folds in avidity. To improve the binding affinity, some amino acids may be mutated back to the original species for enhancement of CDR structural stability. Some critical amino acid residues that may impact antibody bindings may be the upper core region and the interface area (E Stefan, H. Annemarie and P Andreas Methods 34 (2004) 184-199). The following are additional considerations: (i) to avoid most structurally conserved strands of the Fv β-barrel, (it) to rank resurfacing site (mouse amino acid) by relative high surface accessibility (e.g., greater than 30%); and (iii) to classify framework generally reported risk sites.

Humanized AB21 VHB1 (SEQ ID NO:11) and AB21 VLB1 (SEQ ID NO:1S) contain 7 and 2 back mutation amino acids, respectively. (See FIG. 10 and FIGS. 9A and 9B).

Humanized heavy chain, Ha AB21 VHB2 (SEQ ID NO: 12) and Ho AB21 VHB3 (SEQ ID NO: 13) and light chain Hu AB21 VLB2 (SEQ ID NO: 16) contain more back mutation sites. These variants have fewer human framework residues (see FIG. 10).

Example 11. Binding Affinity Analysis of Humanized Antibodies

To confirm the affinity changes after the mouse antibodies were humanized, the variable regions of the humanized light chain and humanized heavy chains were directly generated by the nucleotide synthesis method, respectively. The mouse variable region, humanized regions, and a human Fc chimera antibody expression vector pTCAE8-AB21, were introduced into host cells to prepare recombinant antibody expressing cells. As the host cells for expression, the Free Style™ 293 cells (manufactured by Invitrogen) were used. The vector was introduced into the host cells by polyethylamine (PEI) in accordance with the attached instruction manual (Invitrogen) About 37 μg of the antibody expression vector was linearized by restriction enzymes, the gene was introduced into $3 \times 10^7$ cells.

A culture supernatant containing human IgG antibody was prepared by the method described below. The antibody producing cells were acclimated in a Free Style™ 293 Expression Medium (GIBCO). The cells were cultured in a tissue culture flask, and the culture supernatant was collected when the viable rate of the cells was 90%. The collected supernatant was filtered through 10 μm and 0.2 μm filters (manufactured by Millipore) to remove contaminants. The culture supernatant containing the antibody was affinity-purified using Protein A (manufactured by Millipore), PBS as an absorption buffer, and 20 mM sodium citrate buffer (pH 3.0) as an elution buffer. The elution fractions were adjusted to around pH 6.0 by adding 50 mM sodium phosphate buffer (pH 7.0). The prepared antibody solution was replaced with PBS using a dialysis membrane (10,000 MW cutoff, manufactured by Spectrum Laboratories) and filter-sterilized through a membrane filter (manufactured by Millipore) having a pore size of 0.22 μm to yield the purified antibody. The concentration of the purified antibody was determined by measuring the absorbance at 280 nm and converting the measured value based on 1.45 optical density equaling 1 mg/ml.

Figure 12:
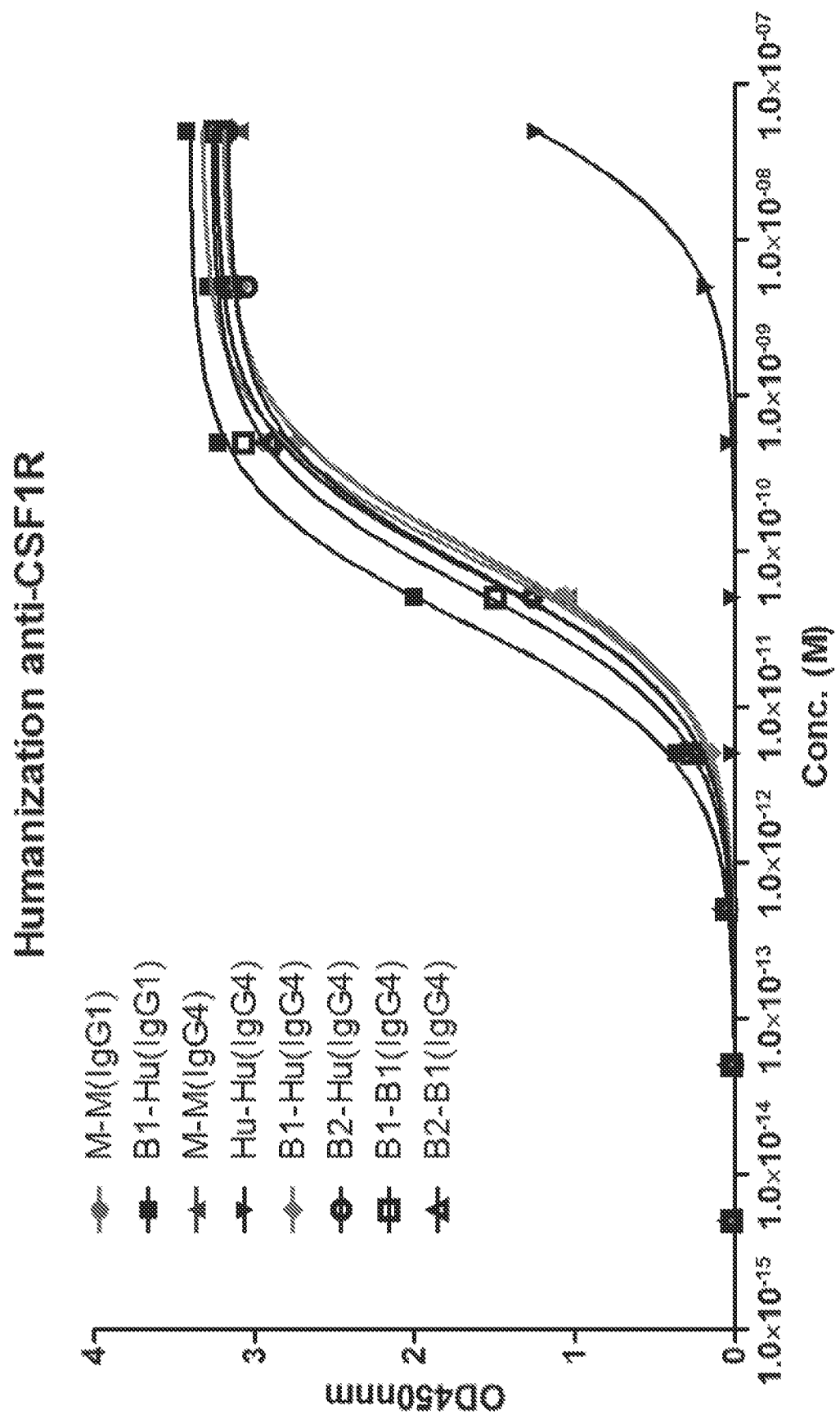
FIG. 12 shows ELISA binding assays of anti CSF-1R variants of the invention.

To know the binding affinity differences among individual antibodies, ELISA method was used. ELISA plate was coated with Jug/ml of CSF1R-ECD-hFc, then add assay antibodies diluted from 50 nM to $1 \times 10^{-5}$ nM (5-10× fold dilution). Assay was measured by adding anti-kappa HRP secondary antibody (1:5000 dilution). Binding curve and KD were determined with GraphPad Prism software using one site-specific binding for nonlinear fit methods. The binding affinity of humanized antibody with heavy chain B1 combined with light chain Hu (B1-Hu) were $9.58 \times 10^{-11}$ M, and heavy chain B1 combined with light chain B1 (B1-B1) was $5.58 \times 10^{-11}$ M, whereas heavy chain Hu combined light chain Hu (Hu-Hu, i.e., the initial humanized antibody) was $8.3 \times 10^{-8}$ M, which is about 1000 folds lower affinity than the affinity of the original mouse antibody (M-M). This loss of avidity was recovered by back mutations, as evidenced by humanized antibodies B1-Hu, B2-Hu, B1-B1, and B2-B1 clones. (See FIG. 11 and FIG. 12). These results also show that any of the heavy chain variants (M, Hu, B1, B2, or B3) may be paired with any of the light chain variant (M, Hu, B1, or B2) to produce an avid antibody.

Example 12. Inhibitory Effects of AB21 mAb on Tumor Growth

In vivo efficacy assay: tumor growth inhibition of anti-CSF-1R antibodies was studied in a colorectal cancer RKO xenograft model in IL 6 NOG mice (Taconic Biosciences, Albany, New York) Because the moose CSF-1R cannot be recognized by anti-human CSF-1R antibody AB21, immunodeficiency mice IL-6 NOG mice engraft with human PBMC were used for efficacy study.

Human PBMC (Lonza, Basel, Switzerland) were engrafted in IL-6 NOG mice (Taconic Biosciences, Albany, New York) 7 days before subcutaneously implant of $1 \times 10^6$ cells of RKO cells (ATCC® CRL-2577™) and 100 µl of Matrigel. Treatment of animals started at day of randomization at a mean tumor volume of 200 mm³. Mice are treated once weekly i.p. with the anti-CSF-1R antibody AB21 mAb (10 mpk or 30 mpk) or combined with biweekly injection of Pembrolizumab (Keytruda®, Merck, 5 mpk), which is an anti-PD-1 antibody. The tumor dimensions are measured by caliper beginning on the staging day and subsequently 2 times per week during the whole treatment period. Tumor volume is calculated according to NCI protocol (Tumor volume=½ab², where "a" and "b" are the long and the short diameters of the tumor, respectively).

Tumor growth analysis is shown in FIG. 13. Inhibition of RKO tumor growth by anti-CSF-1R AB21 mAb (30 mpk, weekly) was similar to the effect of Pembrolizumab (5 mpk, biweekly). Inhibition of RKO tumor growth with the anti-CSF-1R AB21 mAb combined with anti-PD-1 antibody (Pembrolizumab) was statistically more efficacious, suggesting a synergistic effect. These results clearly show that anti-CSF-1R antibodies of the invention would be effective in treating CSF-1R mediated diseases, such as cancer, or an inflammatory or immunological disease. The CSF-1R-mediated cancers include multiple myeloma, acute myeloid leukemia (AML), chronic myeloid leukemia (CML), prostate cancer, breast cancer, ovarian cancer, melanoma, glioblastoma multiforme, giant cell tumor of bone, non-small-cell lung cancers, giant cell tumor of the tendon sheath, renal cancer, metastasis of tumors to other tissues, myelofibrosis, and gastrointestinal stromal tumor. The CSF-1R-mediated inflammatory or immunological diseases include pigmented villonodular synovitis (PVNS), osteoporosis, inflammatory arthritis, or other inflammatory bone erosion.

Embodiments of the invention have been described with reference to limited examples. One skilled in the art would appreciate that these examples are for illustration only and are not meant to limit the scope of the invention and that other modifications and variations are possible without departing from the scope of the invention. Therefore, the scope of the invention should only be limited by the attached claims.

REFERENCES

1. Arango Duque G, Descoteaux A. Macrophage cytokines: involvement in immunity and infectious diseases. Front Immunol 2014; 5: 491
2. Mantovani A, Sozzani S, Locati M, Allavena P, Sica A. Macrophage polarization: tumor-associated macrophages as a paradigm for polarized M2 mononuclear phagocytes. Trends Immunol. 2002; 23(11):549-55
3. Pollard J W, Role of colony-stimulating factor-1 in reproduction and development. Mol. Reprod. Dev. 1997, 46: 54-61
4. Dai X M, Ryan G R, Hapel A J, Dominguez M G, Russell R G, Kapp S, Sylvestre V, Stanley E R, Blood. 2002, 99: 111-120
5. Arango Duque G, Descoteaux A. Macrophage cytokines: involvement in immunity and infectious diseases. Front Immunol 2014; 5: 491.
6. Allavena, P., Sica, A., Solinas, G., Porta, C., Mantovani, A., The inflammatory micro-environment in tumor progression: the role of tumor-associated macrophages. Crit. Rev. Oncol. Hematol. 2008:66, 1.
7. Mantovani, A., Bottazzi, B., Colotta, F., Sozzani, S., Ruco, L., The origin and function of tumor-associated macrophages. Immunol. Today 1992:13, 265.
8. Stanley E R, Chitu V CSF-1 receptor signaling in myeloid cells. Cold Spring Harb Perspect Biol 2014; 6.
9. Pedersen M B, Danielsen A V, Hamilton-Dutoit S J, Bendix K, Norgaard P, Moller M B, Steiniche T, d'Amore F. High intratumoral macrophage content is an adverse prognostic feature in anaplastic large cell lymphoma. Histopathology. 2014; 65:490.
10. Zhang Q W, Liu L, Gong C Y, Shi H S, Zeng Y H, Wang X Z, Zhao Y W, Wei Y Q. Prognostic significance of tumor-associated macrophages in solid tumor: a Meta-analysis of the literature. PLOS One. 2012; 7:e50946. Wan, P. T. C., et al., Mechanism of Activation of the RAF-ERK Signaling Pathway by Oncogenic Mutations of B-RAF. Cell, 2004. 116(6):855
11. Chockalingam S, Ghosh S S. Macrophage colony-stimulating factor and cancer: a review. Tumour Biol, 2014, 35: 10635-10644.
12. Stanley E R. The macrophage colony-stimulating factor, CSF-1. Methods Enzymol, 1985, 116: 564-587.
13. Laoui D, Van Overmeire E, De Baetselier P, Van Ginderachter J A, Raes G. Functional relationship between tumor-associated macrophages and macrophage colony-stimulating factor as contributors to cancer progression. Front Immunol, 2014, 5: 489
14. Joyce J A, Pollard J W. Microenvironmental regulation of metastasis. Nat Rev Cancer, 2009, 9:239-252.
15. Qian B Z, Pollard J W. Macrophage diversity enhances tumor progression and metastasis. Cell, 2010, 141: 39-51.
16. Strachan D C, Ruffell B, Oei Y, Bissell M J, Coussens L M, Pryer N, Daniel D. CSF1R inhibition delays cervical and mammary tumor growth in murine models by attenuating the turnover of tumor-associated macrophages and enhancing infiltration by CD8 T cells. Oncoimmunology, 2013, 2: e26968.
17. Noy R, Pollard J W. Tumor-associated macrophages: from mechanisms to therapy. Immunity, 2014, 41: 49-61.

18. Zhu Y, Knolhoff B L, Meyer M A, Nywening T M, West B L, Luo J, Wang-Gillam A, Goedegebuure S P, Linehan D C, DeNardo D G. CSF1/CSF1R blockade reprograms tumor-infiltrating macrophages and improves response to T-cell checkpoint immunotherapy in pancreatic cancer models. Cancer Res, 2014, 74: 5057-5069.

19. Pyonteck S M, Akkari L, Schuhmacher A J, Bowman R L, Sevenich L, Quail D F, Olson O C, Quick M L, Huse J T, Teijeiro V, Setty M, Leslie C S, Oei Y, Pedraza A, Zhang J, Brennan C W, Sutton J C, Holland E C, Daniel D, Joyce J A. CSF-1R inhibition alters macrophage polarization and blocks glioma progression. Nat Med, 2013, 19: 1264-1272.

20. Mitchem J B, Brennan D J, Knolhoff B L, Belt B A, Zhu Y, Sanford D E, Belaygorod L, Carpenter D, Collins L, Piwnica-Worms D, Hewitt S, Udupi G M, Gallagher W M, Wegner C, West B L, Wang-Gillam A, Goedegebuure P, Linehan D C, DeNardo D G. Targeting tumor-infiltrating macrophages decreases tumor-initiating cells, relieves immunosuppression, and improves chemotherapeutic responses. Cancer Res, 2013, 73: 1128-1141.

The invention claimed is:

1. An antibody, or an antigen-binding fragment thereof, that binds specifically to human CSF-1R, comprising:
   a heavy chain variable domain comprising a HCDR1 region having the sequence of SEQ ID NO: 4, a HCDR2 region having the sequence of SEQ ID NO: 5, and a HCDR3 region having the sequence of SEQ ID NO: 6; and
   a light chain variable domain comprising a LCDR1 region having the sequence of SEQ ID NO: 7, a LCDR2 region having the sequence of SEQ ID NO: 8, and a LCDR3 region having the sequence of SEQ ID NO: 9.

2. The antibody, or the antigen-binding fragment thereof, according to claim 1, wherein the heavy chain variable domain comprises the sequence of SEQ ID NO: 2, 10, 11, 12, or 13, or a sequence having at least 95% homology to the sequence of SEQ ID: 2, 10, 11, 12, or 13, and wherein the light chain variable domain comprises the sequence of SEQ ID NO: 3, 14, 15, or 16, or a sequence having at least 95% homology to the sequence of SEQ ID: 3, 14, 15, or 16.

3. The antibody, or the antigen-binding fragment thereof, according to claim 1, wherein the heavy chain variable domain comprises the sequence of SEQ ID NO: 2, 10, 11, 12, or 13, and wherein the light chain variable domain comprises the sequence of SEQ ID NO: 3, 14, 15, or 16.

4. The antibody, or the antigen-binding fragment thereof, according to claim 1, wherein the antibody, or the antigen-binding fragment thereof, binds specifically to an epitope in an extracellular domain of human CSF-1R, wherein the extracellular domain of human CSF-1R has the amino acid sequence of SEQ ID NO: 1, and the epitope has the sequence of: Ser-Val-Asp-Val-Asn-Phe (SEQ ID NO:17).

5. The antibody, or the antigen-binding fragment thereof, according to claim 1, wherein the antibody, or the antigen-binding fragment thereof, inhibits CSF-1-induced signaling, and/or IL-34-induced signaling.

6. The antibody, or the antigen-binding fragment thereof, according to claim 1, wherein the antibody or antigen-binding fragment thereof inhibits CSF-1R signaling.

7. The antibody, or the antigen-binding fragment thereof, according to claim 1, further comprising a drug conjugate covalently linked to the antibody, or the antigen-binding fragment thereof, to form an antibody-drug conjugate (ADC).

8. The antibody, or the antigen-binding fragment thereof, according to claim 1, wherein the antibody, or the antigen-binding fragment thereof, is linked with a second antibody binding fragment to form a bispecific antibody.

9. A pharmaceutical composition for treating a disease mediated by CSF-1R, CSF-1, and/or IL-34, wherein the pharmaceutical composition comprises the antibody, or the antigen-binding fragment thereof, according to claim 1, and a pharmaceutically acceptable carrier.

10. The pharmaceutical composition of claim 9, wherein the disease is cancer.

11. The pharmaceutical composition of claim 10, wherein the cancer is selected from the group consisting of multiple myeloma, acute myeloid leukemia (AML), chronic myeloid leukemia (CML), prostate cancer, breast cancer, ovarian cancer, melanoma, glioblastoma multiforme, giant cell tumor of bone, non-small-cell lung cancers, giant cell tumor of the tendon sheath, renal cancer, metastasis of tumors to other tissues, myelofibrosis, and gastrointestinal stromal tumor.

12. The pharmaceutical composition of claim 9, the disease is an inflammatory or immunological disease.

13. The pharmaceutical composition of claim 12, wherein the inflammatory or immunological disease is pigmented villonodular synovitis (PVNS), osteoporosis, inflammatory arthritis, or other inflammatory bone erosion.

14. A method for treating a disease mediated by CSF-1R, CSF-1, and/or IL-34, comprising: administering to a subject in need thereof a therapeutically effective amount of the pharmaceutical composition according to claim 9.

* * * * *

SEQUENCE LISTING

```
<160> NUMBER OF SEQ ID NOS: 23

<210> SEQ ID NO 1
<211> LENGTH: 512
<212> TYPE: PRT
<213> ORGANISM: homo sapiens

<400> SEQUENCE: 1

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
                35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
                100                 105                 110

Gln Glu Val Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
    130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Leu Asn Leu Ser
```

```
                    290                 295                 300
Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
                340                 345                 350

Asn Ala Thr Thr Lys Asp Thr Tyr Arg His Thr Phe Thr Leu Ser Leu
                355                 360                 365

Pro Arg Leu Lys Pro Ser Glu Ala Gly Arg Tyr Ser Phe Leu Ala Arg
370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
                420                 425                 430

Gln Cys Ser Gly His Thr Asp Arg Cys Asp Glu Ala Gln Val Leu Gln
                435                 440                 445

Val Trp Asp Asp Pro Tyr Pro Glu Val Leu Ser Gln Glu Pro Phe His
                450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
                500                 505                 510

<210> SEQ ID NO 2
<211> LENGTH: 123
<212> TYPE: PRT
<213> ORGANISM: mus musculus

<400> SEQUENCE: 2

Glu Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
                20                  25                  30

Asn Met Asn Trp Val Lys Gln Ser Asn Gly Lys Ser Leu Glu Trp Ile
            35                  40                  45

Gly Asn Ile Asp Pro Tyr Tyr Gly Thr Thr Tyr Asn Gln Lys Phe
        50                  55                  60

Lys Gly Lys Ala Thr Leu Thr Val Asp Lys Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Arg Gly Asp Tyr Ser Gly Ser Ser Tyr Trp Tyr Phe Asp Val
                100                 105                 110

Trp Gly Ala Gly Thr Thr Val Thr Val Ser Ser
            115                 120

<210> SEQ ID NO 3
<211> LENGTH: 107
<212> TYPE: PRT
<213> ORGANISM: Mus musculus
```

<400> SEQUENCE: 3

Asp Ile Gln Met Thr Gln Ser Ser Tyr Leu Ser Val Ser Leu Gly
1               5                   10                  15

Gly Arg Val Thr Ile Thr Cys Lys Ala Ser Asp His Ile Asn Asn Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Val Thr Tyr Tyr Cys Gln Gln Tyr Trp Ser Thr Pro Phe
                85                  90                  95

Thr Phe Gly Ser Gly Thr Lys Leu Glu Ile Lys
            100                 105

<210> SEQ ID NO 4
<211> LENGTH: 10
<212> TYPE: PRT
<213> ORGANISM: Mus musculus

<400> SEQUENCE: 4

Gly Tyr Ser Phe Thr Gly Tyr Asn Met Asn
1               5                   10

<210> SEQ ID NO 5
<211> LENGTH: 17
<212> TYPE: PRT
<213> ORGANISM: Mus musculus

<400> SEQUENCE: 5

Asn Ile Asp Pro Tyr Tyr Gly Gly Thr Thr Tyr Asn Gln Lys Phe Lys
1               5                   10                  15

Gly

<210> SEQ ID NO 6
<211> LENGTH: 13
<212> TYPE: PRT
<213> ORGANISM: Mus musculus

<400> SEQUENCE: 6

Gly Asp Tyr Ser Gly Ser Ser Tyr Trp Tyr Phe Asp Val
1               5                   10

<210> SEQ ID NO 7
<211> LENGTH: 11
<212> TYPE: PRT
<213> ORGANISM: Mus musculus

<400> SEQUENCE: 7

Lys Ala Ser Asp His Ile Asn Asn Trp Leu Ala
1               5                   10

<210> SEQ ID NO 8
<211> LENGTH: 7
<212> TYPE: PRT
<213> ORGANISM: Mus musculus

<400> SEQUENCE: 8

Gly Ala Thr Ser Leu Glu Thr
1               5

```
<210> SEQ ID NO 9
<211> LENGTH: 9
<212> TYPE: PRT
<213> ORGANISM: Mus musculus

<400> SEQUENCE: 9

Gln Gln Tyr Trp Ser Thr Pro Phe Thr
1               5

<210> SEQ ID NO 10
<211> LENGTH: 123
<212> TYPE: PRT
<213> ORGANISM: Artificial Sequence
<220> FEATURE:
<223> OTHER INFORMATION: Synthetic

<400> SEQUENCE: 10

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ser Phe Thr Gly Tyr
                20                  25                  30

Asn Met Asn Trp Val Gln Ala Pro Gly Lys Gly Leu Glu Trp Met
            35                  40                  45

Gly Asn Ile Asp Pro Tyr Tyr Gly Gly Thr Thr Tyr Asn Gln Lys Phe
        50                  55                  60

Lys Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Arg Gly Asp Tyr Ser Gly Ser Ser Tyr Trp Tyr Phe Asp Val
            100                 105                 110

Trp Gly Gln Gly Thr Leu Val Thr Val Ser Ser
        115                 120

<210> SEQ ID NO 11
<211> LENGTH: 123
<212> TYPE: PRT
<213> ORGANISM: Artificial Sequence
<220> FEATURE:
<223> OTHER INFORMATION: Synthetic

<400> SEQUENCE: 11

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ser Phe Thr Gly Tyr
                20                  25                  30

Asn Met Asn Trp Val Gln Ala Pro Gly Lys Gly Leu Glu Trp Met
            35                  40                  45

Gly Asn Ile Asp Pro Tyr Tyr Gly Gly Thr Thr Tyr Asn Gln Lys Phe
        50                  55                  60

Lys Gly Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Asp Tyr Ser Gly Ser Ser Tyr Trp Tyr Phe Asp Val
            100                 105                 110

Trp Gly Gln Gly Thr Leu Val Thr Val Ser Ser
        115                 120
```

<210> SEQ ID NO 12
<211> LENGTH: 123
<212> TYPE: PRT
<213> ORGANISM: Artificial Sequence
<220> FEATURE:
<223> OTHER INFORMATION: Synthetic

<400> SEQUENCE: 12

```
Glu Val Gln Leu Val Gln Ser Gly Ala Glu Val Lys Lys Pro Gly Ala
1               5                   10                  15

Ser Val Lys Ile Ser Cys Lys Val Ser Gly Tyr Ser Phe Thr Gly Tyr
            20                  25                  30

Asn Met Asn Trp Val Lys Gln Ala Pro Gly Lys Gly Leu Glu Trp Ile
        35                  40                  45

Gly Asn Ile Asp Pro Tyr Tyr Gly Gly Thr Thr Tyr Asn Gln Lys Phe
    50                  55                  60

Lys Gly Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Asp Tyr Ser Gly Ser Ser Tyr Trp Tyr Phe Asp Val
            100                 105                 110

Trp Gly Gln Gly Thr Leu Val Thr Val Ser Ser
        115                 120
```

<210> SEQ ID NO 13
<211> LENGTH: 123
<212> TYPE: PRT
<213> ORGANISM: Artificial Sequence
<220> FEATURE:
<223> OTHER INFORMATION: Synthetic

<400> SEQUENCE: 13

```
Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ala Pro Gly Lys Gly Leu Glu Trp Ile
        35                  40                  45

Gly Asn Ile Asp Pro Tyr Tyr Gly Gly Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Arg Ser Glu Asp Thr Ala Val Tyr Tyr Cys
                85                  90                  95

Ala Arg Arg Gly Asp Tyr Ser Gly Ser Ser Tyr Trp Tyr Phe Asp Val
            100                 105                 110

Trp Gly Gln Gly Thr Leu Val Thr Val Ser Ser
        115                 120
```

<210> SEQ ID NO 14
<211> LENGTH: 107
<212> TYPE: PRT
<213> ORGANISM: Artificial Sequence
<220> FEATURE:
<223> OTHER INFORMATION: Synthetic

<400> SEQUENCE: 14

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Leu
        35                  40                  45

Tyr Gly Ala Thr Ser Leu Glu Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Trp Ser Thr Pro Phe
                85                  90                  95

Thr Phe Gly Gln Gly Thr Lys Val Glu Ile Lys
            100                 105
```

<210> SEQ ID NO 15
<211> LENGTH: 107
<212> TYPE: PRT
<213> ORGANISM: Artificial Sequence
<220> FEATURE:
<223> OTHER INFORMATION: Synthetic

<400> SEQUENCE: 15

```
Asp Ile Gln Met Thr Gln Ser Pro Ser Ser Leu Ser Ala Ser Leu Gly
1               5                   10                  15

Asp Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Leu
        35                  40                  45

Ser Gly Ala Thr Ser Leu Glu Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Trp Ser Thr Pro Phe
                85                  90                  95

Thr Phe Gly Gln Gly Thr Lys Val Glu Ile Lys
            100                 105
```

<210> SEQ ID NO 16
<211> LENGTH: 107
<212> TYPE: PRT
<213> ORGANISM: Artificial Sequence
<220> FEATURE:
<223> OTHER INFORMATION: Synthetic

<400> SEQUENCE: 16

```
Asp Ile Gln Met Thr Gln Ser Pro Ser Ser Leu Ser Ala Ser Leu Gly
1               5                   10                  15

Gly Arg Val Thr Ile Thr Cys Lys Ala Ser Asp His Ile Asn Asn Trp
            20                  25                  30

Leu Ala Trp Tyr Gln Gln Lys Pro Gly Lys Ala Pro Lys Leu Leu Leu
        35                  40                  45

Tyr Gly Ala Thr Ser Leu Glu Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Gln Tyr Trp Ser Thr Pro Phe
                85                  90                  95
```

Thr Phe Gly Ser Gly Thr Lys Leu Glu Ile Lys
        100                 105

<210> SEQ ID NO 17
<211> LENGTH: 6
<212> TYPE: PRT
<213> ORGANISM: Homo sapiens

<400> SEQUENCE: 17

Ser Val Asp Val Asn Phe
1               5

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
gcagcagatc cagggggccag                                              20

<210> SEQ ID NO 19
<211> LENGTH: 18
<212> TYPE: DNA
<213> ORGANISM: Artificial Sequence
<220> FEATURE:
<223> OTHER INFORMATION: Synthetic

<400> SEQUENCE: 19
gtggatagac agatgggg                                                 18

<210> SEQ ID NO 20
<211> LENGTH: 19
<212> TYPE: DNA
<213> ORGANISM: Artificial Sequence
<220> FEATURE:
<223> OTHER INFORMATION: Synthetic

<400> SEQUENCE: 20
gaaatcagac acaccagtg                                                19

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
gtgggagtgg acttgggctg                                               20

<210> SEQ ID NO 22
<211> LENGTH: 25
<212> TYPE: DNA
<213> ORGANISM: Artificial Sequence
<220> FEATURE:
<223> OTHER INFORMATION: Synthetic

<400> SEQUENCE: 22
gatgtctttg gggtagaagt tgttc                                         25

<210> SEQ ID NO 23
<211> LENGTH: 26
<212> TYPE: DNA

```
<213> ORGANISM: Artificial Sequence
<220> FEATURE:
<223> OTHER INFORMATION: Synthetic

<400> SEQUENCE: 23
ctgctcactg gatggtggga agatgg                                          26
```